(12) United States Patent
Murray

(10) Patent No.: US 11,826,489 B2
(45) Date of Patent: Nov. 28, 2023

(54) COLLAGEN SCAFFOLDS

(71) Applicant: The Children's Medical Center Corporation, Boston, MA (US)

(72) Inventor: Martha M. Murray, Sherborn, MA (US)

(73) Assignee: The Children's Medical Center Corporation, Boston, MA (US)

( * ) Notice: Subject to any disclaimer, the term of this patent is extended or adjusted under 35 U.S.C. 154(b) by 0 days.

(21) Appl. No.: 17/519,109

(22) Filed: Nov. 4, 2021

(65) Prior Publication Data

US 2022/0096710 A1 Mar. 31, 2022

Related U.S. Application Data

(60) Division of application No. 16/577,890, filed on Sep. 20, 2019, which is a continuation of application No. 15/679,629, filed on Aug. 17, 2017, now Pat. No. 10,842,914, which is a continuation of application No. 14/765,064, filed as application No. PCT/US2014/014141 on Jan. 31, 2014, now Pat. No. 9,757,495.

(60) Provisional application No. 61/759,868, filed on Feb. 1, 2013.

(51) Int. Cl.
| | |
|---|---|
| A61L 27/24 | (2006.01) |
| A61L 27/56 | (2006.01) |
| A61L 27/36 | (2006.01) |
| C07K 14/78 | (2006.01) |
| C12P 21/00 | (2006.01) |
| A61K 38/00 | (2006.01) |

(52) U.S. Cl.
CPC ........... *A61L 27/24* (2013.01); *A61L 27/3633* (2013.01); *A61L 27/3691* (2013.01); *A61L 27/56* (2013.01); *C07K 14/78* (2013.01); *C12P 21/00* (2013.01); *A61K 38/00* (2013.01); *A61L 2430/06* (2013.01); *A61L 2430/10* (2013.01)

(58) Field of Classification Search
CPC .. A61L 27/24; A61L 27/3633; A61L 27/3691; A61L 27/56; A61L 2430/06; A61L 2430/10; C07K 14/78; C12P 21/00; A61K 38/00

See application file for complete search history.

(56) References Cited

U.S. PATENT DOCUMENTS

| | | |
|---|---|---|
| 2,127,903 A | 5/1936 | Bowen |
| 3,176,316 A | 4/1965 | Bodell |
| 3,195,778 A | 7/1965 | Coates |
| 3,373,906 A | 3/1968 | DeHart et al. |
| 3,545,008 A | 12/1970 | Bader, Jr. |
| 3,587,982 A | 6/1971 | Campbell |
| 3,738,535 A | 6/1973 | Nicholls |
| 3,774,604 A | 11/1973 | Danielsson |
| 3,797,499 A | 3/1974 | Schneider |
| 3,805,300 A | 4/1974 | Tascon-Alonso et al. |
| 3,893,834 A | 7/1975 | Armstrong |
| 4,069,814 A | 1/1978 | Clemens |
| 4,186,448 A | 2/1980 | Brekke |
| 4,187,558 A | 2/1980 | Dahlen et al. |
| 4,255,820 A | 3/1981 | Rothermel et al. |
| 4,265,618 A | 5/1981 | Herskovitz et al. |
| 4,326,540 A | 4/1982 | Bailey et al. |
| 4,400,833 A | 8/1983 | Kurland |
| 4,455,690 A | 6/1984 | Homsy |
| 4,458,678 A | 7/1984 | Yannas et al. |
| 4,467,806 A | 8/1984 | Bhiwandiwala et al. |
| 4,469,101 A | 9/1984 | Coleman et al. |
| 4,483,023 A | 11/1984 | Hoffman, Jr. et al. |
| 4,578,067 A | 3/1986 | Cruz, Jr. |
| 4,584,722 A | 4/1986 | Levy et al. |
| 4,585,458 A | 4/1986 | Kurland |
| 4,610,688 A | 9/1986 | Silvestrini et al. |
| 4,642,119 A | 2/1987 | Shah |
| 4,662,886 A | 5/1987 | Moorse et al. |
| 4,713,075 A | 12/1987 | Kurland |
| 4,731,084 A | 3/1988 | Dunn et al. |
| 4,753,536 A | 6/1988 | Spehar et al. |
| 4,775,380 A | 10/1988 | Seedhom et al. |
| 4,808,184 A | 2/1989 | Tepic |
| 4,808,570 A | 2/1989 | Michaeli |
| 4,846,835 A | 7/1989 | Grande |
| 4,851,513 A | 7/1989 | Devore et al. |
| 4,883,486 A | 11/1989 | Kapadia et al. |
| 4,894,063 A | 1/1990 | Nashef |
| 4,917,699 A | 4/1990 | Chervitz |
| 4,932,942 A | 6/1990 | Maslanka |

(Continued)

FOREIGN PATENT DOCUMENTS

| | | |
|---|---|---|
| CN | 102488713 A | 6/2012 |
| EP | 0295721 A2 | 12/1988 |

(Continued)

OTHER PUBLICATIONS

Magarian et al (The American Journal of Sports Medicine, 2010, vol. 38, No. 12, 2528-2534) (Year: 2010).*
Palmer et al (Materials, 2011, 4, 1469-1482) (Year: 2011).*
Al-Munajjed et al., Development of a collagen calcium-phosphate scaffold as a novel bone graft substitute, Royal College of Surgeons in Ireland, Jan. 1, 2008, 10 pp.
Anseth et al., Photopolymerizable degradable polyanhydrides with osteocompatibility, Nature Biotechnology, Feb. 1999, pp. 156-159, vol. 17.
Arendt et al., Knee Injury Patterns Among Men and Women in Collegiate Basketball and Soccer, the American Journal of Sports Medicine, American Orthopaedic Society for Sports Medicine, 1995, pp. 694-701, Vo. 23, No. 6.

(Continued)

*Primary Examiner* — Sudhakar Katakam
(74) *Attorney, Agent, or Firm* — Offit Kurman, P.A.; Gregory A. Grissett

(57) ABSTRACT

Methods for preparing and using collagen extracts and collagen scaffolds are provided. Additionally, methods and related kits for the repair of articular tissue using the collagen material are provided.

14 Claims, 5 Drawing Sheets

(56) References Cited

U.S. PATENT DOCUMENTS

| | | |
|---|---|---|
| 4,944,755 A | 7/1990 | Hennequin et al. |
| 4,946,377 A | 8/1990 | Kovach |
| 4,955,893 A | 9/1990 | Yannas et al. |
| 4,959,058 A | 9/1990 | Michelson |
| 4,973,321 A | 11/1990 | Michelson |
| 5,007,934 A | 4/1991 | Stone |
| 5,037,396 A | 8/1991 | Streeter |
| 5,078,744 A | 1/1992 | Chvpil |
| 5,078,745 A | 1/1992 | Rhenter et al. |
| 5,119,669 A | 6/1992 | Silvis et al. |
| 5,152,462 A | 10/1992 | Evans |
| 5,171,273 A | 12/1992 | Silver et al. |
| 5,171,274 A | 12/1992 | Fluckiger et al. |
| 5,176,708 A | 1/1993 | Frey et al. |
| 5,197,983 A | 3/1993 | Berman et al. |
| 5,206,023 A | 4/1993 | Hunziker |
| 5,206,028 A | 4/1993 | Li |
| 5,217,495 A | 6/1993 | Kaplan et al. |
| 5,275,826 A | 1/1994 | Badylak et al. |
| 5,281,422 A | 1/1994 | Badylak et al. |
| 5,306,301 A | 4/1994 | Graf et al. |
| 5,370,662 A | 12/1994 | Stone et al. |
| 5,376,118 A | 12/1994 | Kaplan et al. |
| 5,380,087 A | 1/1995 | Haber et al. |
| 5,436,135 A | 7/1995 | Tayot et al. |
| 5,445,833 A | 8/1995 | Badylak et al. |
| 5,455,833 A | 10/1995 | Herre et al. |
| 5,456,721 A | 10/1995 | Legrand |
| 5,458,636 A | 10/1995 | Brancato |
| 5,467,786 A | 11/1995 | Allen et al. |
| 5,474,450 A | 12/1995 | Chronister |
| 5,503,616 A | 4/1996 | Jones |
| 5,522,840 A | 6/1996 | Krajicek |
| 5,549,676 A | 8/1996 | Johnson |
| 5,556,429 A | 9/1996 | Felt |
| 5,595,621 A | 1/1997 | Light et al. |
| 5,652,077 A | 7/1997 | Obinata |
| 5,655,546 A | 8/1997 | Halpern |
| 5,681,353 A | 10/1997 | Li et al. |
| 5,688,276 A | 11/1997 | Shaffer |
| 5,713,374 A | 2/1998 | Pachence et al. |
| 5,749,895 A | 5/1998 | Sawyer et al. |
| 5,756,127 A | 5/1998 | Grisoni et al. |
| 5,800,543 A | 9/1998 | McLeod et al. |
| 5,810,884 A | 9/1998 | Kim |
| 5,855,619 A | 1/1999 | Caplan et al. |
| 5,897,591 A | 4/1999 | Kobayashi |
| 5,902,741 A | 5/1999 | Purchio et al. |
| 5,968,018 A | 10/1999 | Freeman et al. |
| RE36,370 E | 11/1999 | Li |
| 5,993,844 A * | 11/1999 | Abraham ............... A61K 38/39 623/920 |
| 6,007,580 A | 12/1999 | Lehto et al. |
| 6,045,549 A | 4/2000 | Smethers et al. |
| 6,045,569 A | 4/2000 | Kensey et al. |
| 6,080,192 A | 6/2000 | Demopulos et al. |
| 6,087,113 A | 7/2000 | Caplan et al. |
| 6,096,309 A | 8/2000 | Prior et al. |
| 6,117,425 A | 9/2000 | MacPhee et al. |
| 6,129,757 A | 10/2000 | Weadock |
| 6,139,520 A | 10/2000 | McCrory et al. |
| 6,143,029 A | 11/2000 | Rippstein |
| 6,153,292 A | 11/2000 | Bell et al. |
| 6,171,610 B1 | 1/2001 | Vacanti et al. |
| 6,174,333 B1 | 1/2001 | Kadiyala et al. |
| 6,176,880 B1 | 1/2001 | Plouhar et al. |
| 6,203,572 B1 | 3/2001 | Johnson et al. |
| 6,214,047 B1 | 4/2001 | Melvin |
| 6,214,049 B1 | 4/2001 | Garyer et al. |
| 6,234,795 B1 | 5/2001 | Fischer |
| 6,280,474 B1 | 8/2001 | Cassidy et al. |
| 6,283,996 B1 | 9/2001 | Chervitz et al. |
| 6,309,372 B1 | 10/2001 | Fischer et al. |
| 6,365,149 B2 | 4/2002 | Vyakarnam et al. |
| 6,398,761 B1 | 6/2002 | Bills et al. |
| 6,454,129 B1 | 9/2002 | Green |
| 6,472,210 B1 | 10/2002 | Holy et al. |
| 6,517,578 B2 | 2/2003 | Hein |
| 6,592,623 B1 | 4/2003 | Bowlin et al. |
| 6,629,997 B2 | 10/2003 | Mansmann |
| 6,689,153 B1 | 2/2004 | Skiba |
| 6,699,214 B2 | 3/2004 | Gellman |
| 6,946,003 B1 | 9/2005 | Wolowacz et al. |
| 6,964,685 B2 | 11/2005 | Murray et al. |
| 6,971,787 B2 | 12/2005 | Botrie et al. |
| 6,989,034 B2 | 1/2006 | Hammer et al. |
| 7,119,062 B1 | 10/2006 | Alvis et al. |
| 7,148,209 B2 | 12/2006 | Hoemann et al. |
| 7,156,880 B2 | 1/2007 | Evans et al. |
| 7,250,057 B2 | 7/2007 | Forsberg |
| 7,335,220 B2 | 2/2008 | Khosravi et al. |
| 7,652,077 B2 | 1/2010 | Cook et al. |
| 7,838,630 B2 | 11/2010 | Murray et al. |
| 7,901,461 B2 | 3/2011 | Harmon et al. |
| 8,002,813 B2 | 8/2011 | Scarborough et al. |
| 8,070,827 B2 * | 12/2011 | Shortkroff ............... A61L 27/38 623/23.72 |
| 8,137,686 B2 | 3/2012 | Kladakis et al. |
| 8,308,681 B2 | 11/2012 | Slocum et al. |
| 8,642,735 B2 | 2/2014 | Murray et al. |
| 8,652,171 B2 | 2/2014 | Stone et al. |
| 9,308,242 B2 | 4/2016 | Murray |
| 9,314,241 B2 | 4/2016 | Stone et al. |
| 9,414,833 B2 | 8/2016 | Stone et al. |
| 9,757,495 B2 | 9/2017 | Murray |
| 9,849,213 B2 | 12/2017 | Murray |
| 9,918,826 B2 | 3/2018 | Berelsman et al. |
| 9,918,827 B2 | 3/2018 | Berelsman et al. |
| 9,955,980 B2 | 5/2018 | Norton et al. |
| 10,092,288 B2 | 10/2018 | Denham et al. |
| 10,136,886 B2 | 11/2018 | Norton et al. |
| 10,675,016 B2 | 6/2020 | Coleman |
| 10,675,141 B2 | 6/2020 | Greenhalgh et al. |
| 10,702,260 B2 | 7/2020 | Sengun et al. |
| 10,729,430 B2 | 8/2020 | Denham et al. |
| 10,758,644 B2 | 9/2020 | Derwin et al. |
| 10,786,232 B2 | 9/2020 | Murray |
| 10,786,238 B2 | 9/2020 | Murray |
| 10,786,239 B2 | 9/2020 | Murray |
| 10,835,235 B2 | 11/2020 | Coleman |
| 10,842,914 B2 | 11/2020 | Murray |
| 11,076,845 B2 | 8/2021 | Murray |
| 11,076,846 B2 | 8/2021 | Murray |
| 2001/0044659 A1 | 11/2001 | Laboureau et al. |
| 2002/0022884 A1 | 2/2002 | Mansmann |
| 2002/0038151 A1 | 3/2002 | Plouhar et al. |
| 2002/0055749 A1 | 5/2002 | Esnouf et al. |
| 2002/0123805 A1 | 9/2002 | Murray et al. |
| 2002/0161450 A1 | 10/2002 | Doi et al. |
| 2002/0183845 A1 | 12/2002 | Mansmann et al. |
| 2003/0012805 A1 | 1/2003 | Chen et al. |
| 2003/0023316 A1 | 1/2003 | Brown et al. |
| 2003/0033022 A1 | 2/2003 | Plouhar et al. |
| 2003/0078659 A1 | 4/2003 | Yang |
| 2003/0147935 A1 | 8/2003 | Binette et al. |
| 2003/0163144 A1 | 8/2003 | Weadock et al. |
| 2003/0167053 A1 | 9/2003 | Taufig |
| 2003/0212456 A1 | 11/2003 | Lipchitz et al. |
| 2003/0236573 A1 | 12/2003 | Evans et al. |
| 2004/0005297 A1 | 1/2004 | Connelly et al. |
| 2004/0024456 A1 | 2/2004 | Brown, Jr. et al. |
| 2004/0059416 A1 | 3/2004 | Murray et al. |
| 2004/0078077 A1 | 4/2004 | Binette et al. |
| 2004/0170664 A1 | 9/2004 | Spector et al. |
| 2004/0243235 A1 | 12/2004 | Goh et al. |
| 2004/0258729 A1 | 12/2004 | Czernuszka et al. |
| 2004/0262332 A1 | 12/2004 | Pauser et al. |
| 2004/0267362 A1 | 12/2004 | Hwang et al. |
| 2005/0027307 A1 | 2/2005 | Schwartz et al. |
| 2005/0100536 A1 | 5/2005 | Mishra |
| 2005/0129730 A1 | 6/2005 | Pang et al. |
| 2005/0183731 A1 | 8/2005 | Hunter et al. |
| 2005/0192581 A1 | 9/2005 | Molz et al. |
| 2005/0230422 A1 | 10/2005 | Muller et al. |

(56) References Cited

U.S. PATENT DOCUMENTS

| | | |
|---|---|---|
| 2005/0261736 A1 | 11/2005 | Murray et al. |
| 2005/0267521 A1 | 12/2005 | Forsberg |
| 2006/0190041 A1 | 8/2006 | Fallin et al. |
| 2007/0118217 A1 | 5/2007 | Brulez et al. |
| 2007/0150064 A1 | 6/2007 | Ruberte et al. |
| 2007/0269476 A1 | 11/2007 | Voytik-Harbin et al. |
| 2007/0288023 A1 | 12/2007 | Pelligrino et al. |
| 2008/0027542 A1 | 1/2008 | McQuillan et al. |
| 2008/0097430 A1 | 4/2008 | Bernstein et al. |
| 2008/0188936 A1 | 8/2008 | Ball et al. |
| 2008/0195205 A1 | 8/2008 | Schwartz |
| 2008/0228271 A1 | 9/2008 | Stone et al. |
| 2009/0018655 A1 | 1/2009 | Brunelle et al. |
| 2009/0143765 A1 | 6/2009 | Slocum et al. |
| 2009/0171143 A1 | 7/2009 | Chu et al. |
| 2009/0254104 A1 | 10/2009 | Murray |
| 2009/0306776 A1 | 12/2009 | Murray |
| 2010/0106254 A1 | 4/2010 | DelSignore |
| 2010/0221835 A1 | 9/2010 | Tanaka et al. |
| 2010/0298937 A1 | 11/2010 | Laurencin et al. |
| 2011/0027338 A1 | 2/2011 | Murray et al. |
| 2011/0054524 A1 | 3/2011 | Beevers et al. |
| 2011/0184227 A1 | 4/2011 | Altman et al. |
| 2011/0295284 A1 | 12/2011 | Purdue et al. |
| 2011/0306555 A1 | 12/2011 | Murray et al. |
| 2012/0071975 A1 | 3/2012 | Gonzalez-Hernandez |
| 2012/0123474 A1 | 5/2012 | Zajac et al. |
| 2012/0201896 A1 | 8/2012 | Murray et al. |
| 2012/0283831 A1 | 11/2012 | Murray |
| 2013/0231609 A1 | 9/2013 | Slocum et al. |
| 2013/0273017 A1 | 10/2013 | Murray |
| 2013/0345810 A1 | 12/2013 | Jaeger et al. |
| 2014/0039620 A1 | 2/2014 | Cantournet et al. |
| 2014/0134249 A1 | 5/2014 | Murray et al. |
| 2014/0172096 A1 | 6/2014 | Koob et al. |
| 2014/0369984 A1 | 12/2014 | Murray et al. |
| 2015/0088198 A1 | 3/2015 | Spenciner et al. |
| 2015/0359530 A1 | 12/2015 | Moore |
| 2015/0367030 A1 | 12/2015 | Murray |
| 2016/0081790 A1 | 3/2016 | Cournoyer et al. |
| 2016/0206779 A1 | 7/2016 | Murray |
| 2016/0263279 A1 | 9/2016 | Murray et al. |
| 2016/0354195 A1 | 12/2016 | Spenciner |
| 2017/0143551 A1 | 5/2017 | Coleman |
| 2017/0156727 A1 | 6/2017 | Wilson-Wirth et al. |
| 2017/0281327 A1 | 10/2017 | Kaplan et al. |
| 2017/0340772 A1 | 11/2017 | Murray |
| 2017/0360437 A1 | 12/2017 | Ferguson et al. |
| 2018/0207316 A1 | 7/2018 | Murray |
| 2018/0228598 A1 | 8/2018 | Mathisen |
| 2019/0134269 A1 | 5/2019 | Murray et al. |
| 2019/0380693 A1 | 12/2019 | Burkhart |
| 2019/0388582 A1 | 12/2019 | Murray |
| 2020/0000573 A1 | 1/2020 | Whittaker et al. |
| 2020/0009292 A1 | 1/2020 | Murray |
| 2020/0171203 A1 | 6/2020 | Murray |
| 2020/0196998 A1 | 6/2020 | Murray |
| 2020/0196999 A1 | 6/2020 | Murray |
| 2020/0214690 A1 | 7/2020 | Murray |
| 2020/0222586 A1 | 7/2020 | Murray |
| 2020/0253715 A1 | 8/2020 | Trenhaile |
| 2020/0345475 A1 | 11/2020 | Lima et al. |

FOREIGN PATENT DOCUMENTS

| | | |
|---|---|---|
| EP | 0445951 A2 | 9/1991 |
| EP | 0645149 A1 | 3/1995 |
| EP | 1254671 A1 | 11/2002 |
| EP | 1273312 A1 | 1/2003 |
| EP | 3798226 A1 | 3/2021 |
| EP | 4162936 A1 | 4/2023 |
| GB | 2106794 A | 4/1983 |
| WO | 8500511 A1 | 2/1985 |
| WO | 9213565 A1 | 8/1992 |
| WO | 9311723 A1 | 6/1993 |
| WO | 9321857 A1 | 11/1993 |
| WO | 9525550 A1 | 9/1995 |
| WO | 9940771 A1 | 8/1999 |
| WO | 2000047130 A1 | 8/2000 |
| WO | 2000074760 A2 | 12/2000 |
| WO | 2001066130 A1 | 9/2001 |
| WO | 2002067812 A2 | 9/2002 |
| WO | 2003011107 A2 | 2/2003 |
| WO | 2003105737 A1 | 12/2003 |
| WO | 2004078134 A2 | 9/2004 |
| WO | 2006086479 A2 | 8/2006 |
| WO | 2007087353 A2 | 8/2007 |
| WO | 2008036393 A1 | 3/2008 |
| WO | 2008060361 A2 | 5/2008 |
| WO | 2008109407 A2 | 9/2008 |
| WO | 2008109807 A2 | 9/2008 |
| WO | 2010048418 A1 | 4/2010 |
| WO | 2010084481 A1 | 7/2010 |
| WO | 2010108237 A1 | 9/2010 |
| WO | 2013116744 A1 | 8/2013 |
| WO | 2014121067 A1 | 8/2014 |
| WO | 2018009634 A1 | 1/2018 |

OTHER PUBLICATIONS

Authorized Officer Athina Nickitas-Etienne, International Preliminary Report on Patentability, International Patent Application No. PCT/US2014/014141, dated May 13, 2014, 9 pp.

Authorized Officer Athina Nickitas-Etienne, International Preliminary Report on Patentability, International Patent Application No. PCT/US2006/004445, dated Feb. 17, 2009, 4 pp.

Authorized Officer Aurore Schneider, International Search Report and the Written Opinion, International Patent Application No. PCT/US2017/040865, dated Oct. 19, 2017, 8 pp.

Authorized Officer Brian Pellegrino, International Search Report, International Patent Application PCT/US2002/023885, dated Sep. 30, 2002, 3 pp.

Authorized Officer Brian Pellegrino, International Preliminary Examination Report, International Patent Application PCT/US2002/023885, dated Jan. 30, 2003, 3 pp.

Authorized Officer Ellen Moyse, International Preliminary Report on Patentability, International Patent Application No. PCT/US2007/001908, dated Jul. 29, 2008, 9 pp.

Authorized Officer Ellen Moyse, International Preliminary Report on Patentability, International Patent Application No. PCT/US2007/021009, dated Jan. 12, 2010, 13 pp.

Authorized Officer Lee W. Wong, International Search Report and the Written Opinion, International Patent Application No. PCT/US2007/001908, dated Sep. 5, 2007, 10 pp.

Authorized Officer Manuel A. Mendez, International Search Report and the Written Opinion, International Patent Application No. PCT/US2006/004445, dated Jun. 13, 2008, 5 pp.

Authorized Officer Monica Lopez Garcia, International Search Report and the Written Opinion, International Patent Application No. PCT/US2007/021009, dated Sep. 1, 2009, 18 pp.

Authorized Officer Ross Heosey, International Search Report and the Written Opinion, International Patent Application No. PCT/US2013/024467, dated Apr. 29, 2013, 12 pp.

Authorized Officer Shawn Lyons, International Search Report and the Written Opinion, International Patent Application No. PCT/US2014/014141, dated May 13, 2014, 14 pp.

Authorized Officer Simin Baharlou, International Preliminary Report on Patentability, International Patent Application No. PCT/US2017/040865, dated Jan. 8, 2019, 6 pp.

Buck, R.C., Regeneration of Tendon, the Journal of Pathology and Bacteriology, 1953, 22 pp., vol. LXVI, No. I.

Chamberlain et al., Early peripheral nerve healing in collagen and silicone tube implants: Myofibroblasts and the cellular response, Biomaterials 19, Elsevier, 1998, pp. 1393-1403.

Chamberlain et al., Collagen-GAG Substrate Enhances the Quality of Nerve Regeneration through Collagen Tubes up to Level of Autograft, Experimental Neurology 154, 1998, pp. 315-329, American Press.

(56) References Cited

OTHER PUBLICATIONS

Chamberlain, Lila Jo, Long Term Functional and Morphological Evaluation of Peripheral Nerves Regenerated Through Degradable Collagen Implants, MS Thesis, Massachusetts Institute of Technology, 1998, pp. 2.

Crapo et al., An overview of tissue and whole organ decellularization processes, NIH Public Access, Elsevier, Ltd., Biomaterials, Apr. 2011, pp. 3233-3243.

Cross et al., Dense type I collagen matrices that support cellular remodeling and microfabrication for studies of tumor angiogenesis and vasculogenesis in vitro, Biomaterials, 2010, pp. 8596-8507, Elsevier, Ltd.

Deie et al., High intrinsic healing potential of human anterior cruciate ligament, Acta Orthopaedica Scandinavica, 1995, pp. 28-32, vol. 66(1).

Desrosiers et al., Proliferative and Matrix Synthesis Response of Canine Anterior Cruciate Ligament Fibroblasts Submitted to Combined Growth Factors, Journal of Orthopaedic Research, the Journal of Bone and Joint Surgery, Inc., 1996, pp. 200-208, vol. 14, No. 2.

Dye, Scott F. MD, The Future of Anterior Cruciate Ligament Restoration, Clinical Orthopaedics and Related Research, Apr. 1996, pp. 130-139, vol. 325.

Extended European Search Report, European Patent Application No. 13743583.0, dated Sep. 17, 2015, 7 pp.

Extended European Search Report, European Patent Application No. 06720499.0, Completed Jul. 7, 2009, 7 pp.

Australian Examination Report, Australian Patent Application 2017254864, dated Aug. 31, 2018, 7 pp.

Partial European Search Report, European Patent Application 14745975.4, dated Aug. 26, 2016, 7 pp.

International Preliminary Report on Patentability, PCT/US2013/024467, dated Aug. 5, 2014, 7 pp.

Faryniarz et al., Myofibroblasts in the Healing Lapine Medical Collateral Ligament: Possible Mechanisms of Contraction, Journal of Orthopaedic Research, the Journal of Bone and Joint Surgery, Inc., 1996, pp. 228-238, vol. 14, No. 2.

Ferber, Dan, Lab-Grown Organs Begin to Take Shape, Science, Apr. 1999, 6 pp., the American Association for the Advancement of Science, vol. 284, No. 5413.

Ferber, Dan, Tissue Engineering: From the Lab to the Clinic, Science, Apr. 1999, 2 pp., the American Association for the Advancement of Science, vol. 284, No. 5413.

Ford et al., Autologous Collagen Vocal Fold Injection: a Preliminary Clinical Study, Sep. 1995, 944-948, Laryngoscope 105.

Frank et al., Natural History of Healing in the Repaired Medial Collateral Ligament, Journal of Orthopaedic Research, Orthopaedic Research Society, 1983, pp. 179-188, vol. 1, No. 2.

Geiger, et al., An In Vitro Assay of Anterior Cruciate Ligament (ACL) and Medial Collateral Ligament (MCL) Cell Migration, Connective Tissue Research, 1994, pp. 215-224, vol. 30. Gordon and Breach Science Publishers, S.A.

Gerich et al., Gene transfer to the patellar tendon, Knee Surg., Sports Traumatol, Arthroscopy, 1998, pp. 118-123, Springer-Verlag.

Gwinn et al., Relative Gender Incidence of Anterior Cruciate Ligament Injury at a Military Service Academy, 66th Annual Meeting of the American Academy of Orthopaedic Surgeons, Anaheim, CA, 1999, 1 pp., Paper No. 143.

Hefti et al., Healing of the Transected Anterior Cruciate Ligament in the Rabbit, the Journal of Bone and Joint Surgery, Mar. 1991, pp. 373-383, vol. 73-A, No. 3.

Itoh et al., Characterization of CO3AP-collagen sponges using X-ray high-resolution microtomography, Biomaterials, 2004, pp. 2577-2583, vol. 25.

Jackson et al., Biologic remodeling after anterior cruciate ligament reconstruction using a collagen matrix derived from demineralized bone: an experimental study in the goat model, the American Journal of Sports Medicine, Jul.-Aug. 1996, 15 pp., vol. 24, No. 4.

Juncosa-Melvin et al., The Effect of Autologous Mesenchymal Stem Cells on the Biomechanics an Histology of Gel-Collagen Sponge Constructs Used for Rabbit Patellar Tendon Repair, Tissue Engineering, 2006, pp. 370-380, vol. 12.

Kanungo et al., Density-property relationships in mineralized collagen-glycosaminoglycan scaffolds, Aug. 26, 2008, pp. 1006-1018, Acta Biomaterials 5, Elsevier.

Kato et al., Formation of continuous collagen fibres: evaluation of biocompatibility ad mechanical properties, Biomaterials, Apr. 1990, pp. 169-175, vol. 11, Butterworth & Co., Ltd (Publishers).

Kawamoto et al., Selective migration of alpha-smooth muscle actin-positive myofibroblasts toward fibronectin in the Boyden's blindwell chamber, Clinical Science, 1997, pp. 355-362, vol. 93.

Kliment et al., A novel method for accurate collagen and biochemical assessment of pulmonary tissue utilizing one animal, Int. J. Clin. Exp. Pathol., 2011, pp. 349-355.

Louie, Libby K., Effect of a Porous Collagen-Glycosaminoglycan copolymer on Early Tendon Healing in a Novel Animal Model, Jan. 10, 1997, 1 pp., Ph.D. Thesis, Massachusetts Institute of Technology.

Louie et al., Development of a Collagen-GAG Copolymer Implant for the Study of Tendon Regeneration, Materials Research Society Symposium Proceedings, 1994, pp. 19-24, vol. 331.

Louie et al., Healing of Tendon Defects Implanted with a Porous Collagen=GAG Matrix: Histological Evaluation, Tissue Engineering, 1997, pp. 187-195, vol. 3, No. 2.

Marshall et al., The Anterior Ligament Cruciate Ligament: a Technique of Repair and Reconstruction, Clinical Orthopaedics and Related Research, Sep. 1979, pp. 97-106, No. 143.

Masur et al., Myofibroblasts differentiate from fibroblasts when plated at low density, Proc. Natl. Acad. Sci. USA, Apr. 1996, pp. 4219-4223, Cell Biology, vol. 93.

Murray et al., Migration of Human Anterior Cruciate Ligament Fibrosis Into Porous Collagen-GAG Matrices In Vitro, 24th Annual Meeting of the Society for Biomaterials, San Diego, CA, Apr. 22-26, 1996, pp. 463.

Murray et al., The Migration of Human Anterior Cruciate Ligament Fibroblasts Into Porous Collagen-GAG Matrices In Vitro, 45th Annual Meeting, Orthopaedic Research Society, Anaheim, CA, Feb. 1-4, 1999, 1 pp.

Murray et al., Differences in the Outgrowth of Cells from Explants from the Proximal and Distal Human ACL and Responses to TGF-B1,47th Annual Meeting, Orthopaedic Research Society, San Francisco, CA, Feb. 25-28, 2001, pp. 0788.

Murray et al., The Effects of Selected Growth Factors on Human ACL Cell Interactions with 3-D Collagen-GAG Scaffolds, 47th Annual Meeting, Orthodaedic Research Society, San Francisco, CA, Feb. 25-28, 2001, pp. 0790.

Murray et al., The migration of cells from the ruptured human anterior cruciate ligament into collagen-glycosaminoglycan regeneration templates in vitro, Biomaterials 22, 2001 Elsevier, pp. 2393-2402.

Murray et al., The Effect Ruptured Human Anterior Cruciate Ligament Histology on Cell Interactions with a Collagen-GAG Scaffold In Vitro, Davos Tissue Engineering Workshop, Davos Switzerland, 2000, I pp.

Murray et al., Histological Changes in the Human Anterior Cruciate Ligament After Rupture, the Journal of Bone and Joint Surgery Incorporated, Oct. 2000, pp. 1387-1397, vol. 82-A, No. 10.

Murray et al., Fibroblast Distribution in the Anteromedial Bundle of the Human Anterior Cruciate Ligament: the Presence of alpha smooth muscle actin-positive cells, J. Orthop. Res., 1999, pp. 18-27, vol. 17., No. 1.

Murray et al., Migration os Cells from Human Anterior Cruciate Ligament Explants into Collagen-Glycosaminoglycan Scaffolds, Journal of Orthopaedic Research, 2000, pp. 557-564, vol. 18, No. 4.

Murray et al., Migration of Cells fro mRuptured Human Anterior Curciate Ligament Explants Into Collagen-GAG Matrices, 6th World Biomatrials Conference, Kamuela, HI, 2000, 1 pp.

Murray et al., Use of a Collagen-Platelet Rich Plasma Scaffold to Stimulate Healing of a Central Defect in the Canine ACL, Journal of Orthopaedic Research, Apr. 2006, pp. 820-830, Wilet InterScience.

(56) References Cited

OTHER PUBLICATIONS

Nakamura et al., A Comparison of in vivo gene delivery methods for antisense therapy in ligament healing, Gene Therapy, 1998, pp. 1455-1461, vol. 5.
Nakamura et al., Early biological effect of in vivo gene transfer of platelet-derived growth factor (PDGF)-B into healing patellar ligament, Gene Therapy, 1998, pp. 1165-1170, vol. 5.
Neuman et al. The Determination of Hydroxyproline, J. Biol. Chem, 184, 1950, pp. 299-306.
Niklason et al., Functional arteries grown in vitro, Copyright American Association for the Advancement of Science, Washington, Apr. 16, 1999, 6 pp.
[No Author Listed], Guidance Document for Testing Biodegradable Polymer Implant Devices, ODE Guidance Documents, Apr. 20, 1996, 11 pp.
Noyes et al., Bone-Patellar Ligament-Bone and Fascia Lata Allografts for Reconstruction of the Anterior Cruciate Ligament, the Journal of Bone and Joint Surgery, 1990, pp. 1125-1136, vol. 72-A, No. 8.
Officer Anita Meacle, European Office Action, European Patent Application No. 07 867 174.0, dated Nov. 29, 2018, 5 pp.
Peter et al., Synthesis of poly (propylene fumarate) by acylation of propylebe glycol in the presence of a proton scavenger, Journal of Biomaterial Science, Polymer Edition, 1999, pp. 363-373, vol. 10, No. 3.
Qui et al. Outgrowth of chondrocytes from human articular cartilage explants and ecpression of alpha-smooth muscle actin, Wound Repair an d Regeneration, Sep.-Oct. 2000, pp. 383-391, vol. 8, No. 5.
Sadowska et al., Isolation of collagen from the skins of Baltic cod (Gadus morhua), Food Chemistry, 2003, pp. 257-262, Elsevier Science, Ltd.
Schmidt et al., Effect of Growth Factors on the Proliferation of Fibroblasts from the Medical Collateral and Anterior Cruciate Ligaments, Journal of Orthopaedic Research, the Journal of Bone and Joint Surgert, Inc., 1995, pp. 184-190, vol. 13, No. 2.
Schulz Torres et al., Effects of Modulus of Elasticity of Collagen Sponges on Their Cell-Medicated Contraction In Vitro, Massachusetts Institute of Technology, Jun. 1998, 96 pp.
Spindler et al., Comparison of Collagen Synthesis in the Peripheral and Central Region of the Canine Meniscus, Clinical Orthopaedics, Jun. 1994, pp. 256-263, vol. 303.
Spindler et al., Regional Mitogenic Response of the Meniscus to Platelet-Derived Growth Factor (PDGF-AB), Journal of Orthopaedic Research, the Journal od Bone and Joint Surgery, Inc., 1995, pp. 201-207, vol. 13, No. 2.
Spindler et al., Patellar Tendon and Anterior Cruciate Ligament Have Different Mitogenic Responses to Platelet-Derived Growth Factor and Transforming Growth Factor Beta, Journal of Orthpaedic Research, the Journal of Bone and Joint Surgery, Inc., 1996, pp. 542-546, vol. 14, No. 4.
Stensel et al., Collagen as a Biomaterial, Annual Review Biophysics Bioenginering, 1974, 24 pp.
Stevenson et al., Gender Differences in Knee Injury Epidemiology Among Competitive Alpine Ski Racers, the Iowa Orthopaedic Journal, 1998, pp. 64-66, vol. 18.
Stone et al., Future Directions Collagen-Based Prosteses for Meniscal Regeneration, Clinical Orthopaedics and Related Research, Mar. 1990, pp. 129-136, No. 252.
Stone et al., Regeneration of Meniscal Cartilage with Use of a Collagen Scaffold, the Journal of Bone and Joint Surgery, Incorporated, Dec. 1997, pp. 1770-1777, vol. 79-A, No. 12.
Suggs et al., Platelet adhesion on a bioresorbable poly (propylene fumarate-co-ethylene glycol) copolymer, Biomaterials 20, 1999, pp. 683-690, Elsevier Science Ltd.
Troxel, Karen S., Delay of Skin Would Contraction by Porous Collagen-GAG Matrices, (Ph.D. Thesis, Massachusetts Institute of Technology), 1994, 1 pp.
Weadock et al., Physical crosslinking of collagen fibers: Comparison of ultraviolet irradiation and dehydrothermal treatment, Journal of Biomedical Materials Research, 1995, pp. 1373-1379, vol. 29.
Witkowski et al., Migration and Healing of Ligament Cells under Inflammatory Conditions, Journal of Orthopaedic Research, the Journal of Bone and Joint Surgery, Inc., 1997, pp. 269-277, vol. 15, No. 2.
Yannas, Ioannis V., Models of Organ Regeneration Processes Induced by Templates, Bioartificial Organs: Science, Medicine and Technology, 1997, pp. 280-293, the New York Academy of Sciences, New York, NY.
Yannas, Ioannis V., Regeneration of Skin and Nerve by Use of Collagen Templates, Collagen, Sep. 23, 2002, pp. 87-115, vol. III, No. 3345.
Yannas et al., Polymeric Template Facilitates Regeneration of Sciatic Nerve Across, the 11th Annual Meeting of the Society for Biomaterials, San Diego, CA, Apr. 25-28, 1985, pp. 146.
Yannas et al., Synthesis and characterization of a model extracellular matrix that induces partial regeneration of adult mammalian skin, Developmental Biology, Proc. Nat'l. Acad. Sci. USA, Feb. 1989. pp. 933-937, vol. 86, No. 3.
Extended European Search Report, European Patent Application No. EP 20195319, Report Completion Date Feb. 22, 2021, 11 pp.
Magarian et al., Delay of 2 or 6 Weeks Adversely Affects the Functional Outcome of Augmented Primary Repair of the Porcine Anterior Cruciate Ligament, the American Journal of Sports Medicine, vol. 38, No. 12, Nov. 12, 2010, pp. 2528-2534.
Website: https://www.reprocell.com/product-catalog/koken-atelocollagen/atelocollagen-bovine-dermis-acidic-solution, pp. 1-3, retrieved May 28, 2021 Antelocollagen Type I Acidic Solution (AteloCell) (Year: 2021).

\* cited by examiner

COLLAGEN SCAFFOLDS

CROSS-REFERENCE TO RELATED APPLICATIONS

This application is a divisional of U.S. application Ser. No. 16/577,890, filed Sep. 20, 2019, is continuation of U.S. application Ser. No. 15/679,629, filed Aug. 17, 2017, now U.S. Pat. No. 10,842,914, issued Nov. 24, 2020, which is continuation of U.S. application Ser. No. 14/765,064, filed Jul. 31, 2015, now U.S. Pat. No. 9,757,495, issued Sep. 12, 2017, which is national stage entry under 35 U.S.C. 371 of PCT Application No. PCT/US2014/014141, filed Jan. 31, 2014, which claims priority under 35 U.S.C. § 119(e) to U.S. provisional patent application Ser. No. 61/759,868, filed Feb. 1, 2013, and entitled Collagen Scaffolds. The entire contents of each application listed in this paragraph are incorporated herein by reference.

BACKGROUND OF THE INVENTION

While the body has efficient processes for healing most damaged tissue, tissue such as intra-articular tissue often fails to heal after an injury. The tissue outside of joints heals by forming a fibrin clot, which connects the ruptured tissue ends and is subsequently remodeled to form scar, which heals the tissue. Inside a synovial joint, a fibrin clot either fails to form or is quickly lysed after injury to the knee, thus preventing joint arthrosis and stiffness after minor injury. Joints contain synovial fluid which, as part of normal joint activity, naturally prevent clot formation in joints. This fibrinolytic process results in premature loss of the fibrin clot scaffold and disruption of the healing process for tissues within the joint or within intra-articular tissues. Enhancing healing of ligaments using growth factors has been an area of great interest and research.

SUMMARY OF THE INVENTION

The invention relates in some aspects to methods for preparing and using collagen extracts and scaffolds and related products.

In some aspects the invention is a method for preparing a collagen extract. The method involves one or more of the steps of animal tissue dissection, freeze drying, such as lyophilization, salt extraction, water rinse and detergent treatment, PBS rinse and wash, enzyme digestion, PBS/EDTA wash, water rinse and citrate buffer, and ultracentrifugation and acid solubilization.

Once the collagen extract is prepared the collagen scaffold can be made using the collagen extract.

In some embodiments, the animal tissue dissection involves retrieval of tissues from porcine, ovine, bovine or human knees. In some embodiments, the animal tissue dissection involves retrieval of tissue either from fresh or previously frozen (and then thawed) knees (from age specific animals with skin on to maintain sterility). In other embodiments the knee connective tissue is dissected from fresh and skin-on knees under sterile conditions. If the dissection is from fresh knees the tissue may be frozen before the first step. In some embodiments, the tissue harvested is dermis. In some embodiments, the tissue harvested is subdermal tissue. In some embodiments, the tissue harvested is adipose tissue. In some embodiments, the tissue harvested is bursal tissue. In some embodiments, the tissue harvested is joint capsule. In some embodiments, the tissue harvested is ligament. In some embodiments, the tissue harvested is tendon. In some embodiments, the tissue harvested is cartilage. In some embodiments, the tissue harvested is meniscus. In some embodiments, the tissue harvested is muscle. In some embodiments, the tissue harvested is subdermal muscle fascia.

In some embodiments, the animal tissue dissection involves retrieval of tissues from porcine, ovine, bovine or human knees. In some embodiments, the animal tissue dissection involves retrieval of tissue either from fresh or previously frozen (and then thawed) knees (from age specific animals with skin on to maintain sterility). In other embodiments the knee connective tissue is dissected from fresh and skin-on knees under sterile conditions. If the dissection is from fresh knees the tissue may be frozen before the first step. In some embodiments, the tissue harvested is dermis. In some embodiments, the tissue harvested is subdermal tissue. In some embodiments, the tissue harvested is adipose tissue. In some embodiments, the tissue harvested is bursal tissue. In some embodiments, the tissue harvested is joint capsule. In some embodiments, the tissue harvested is ligament. In some embodiments, the tissue harvested is tendon. In some embodiments, the tissue harvested is cartilage. In some embodiments, the tissue harvested is meniscus. In some embodiments, the tissue harvested is muscle. In some embodiments, the tissue harvested is subdermal muscle fascia.

DETAILED DESCRIPTION OF THE INVENTION

Figure 1:
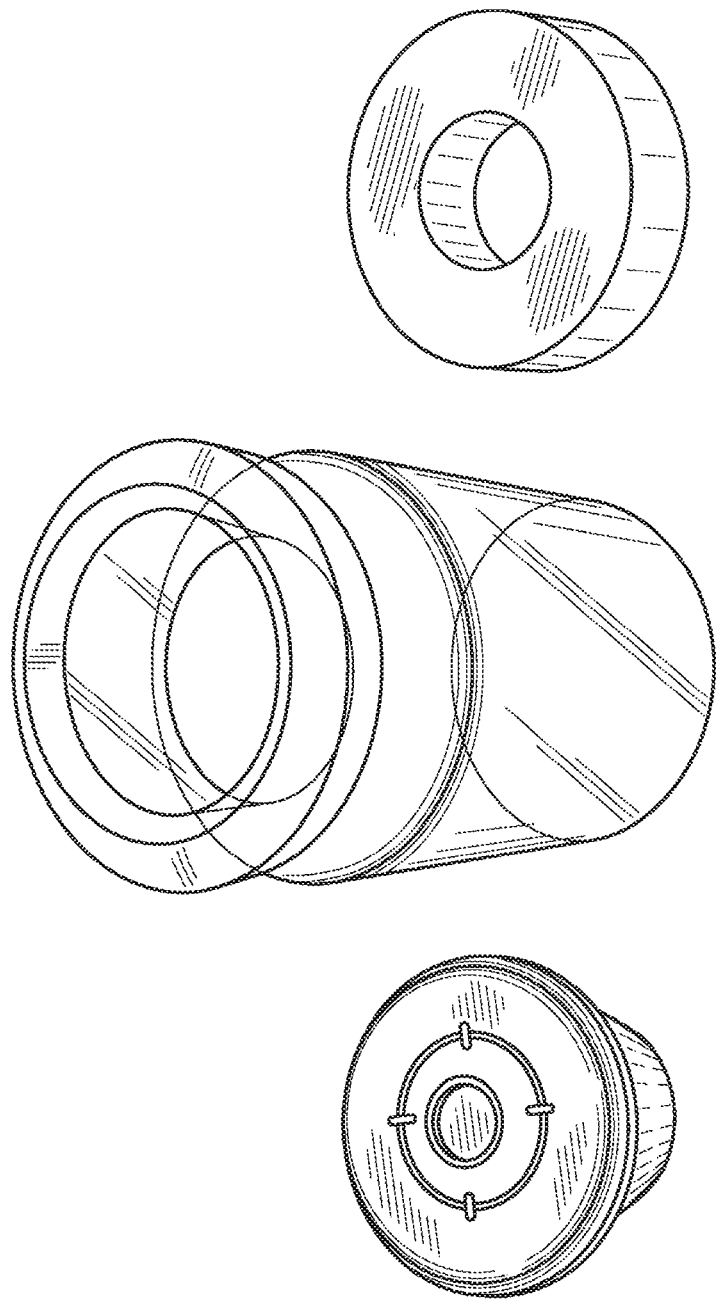
FIG. 1 is a photograph showing initial packaging set up of an ECM Scaffold (e.g., a collagen scaffold) for e-beam testing.

The invention involves, in some aspects, methods for preparing collagen extracts. A detailed protocol for the method is provided below. The collagen extracts prepared according to the methods have superior properties to collagen extracts prepared according to other methods and are particularly useful as a collagen source for preparing tissue scaffolds. The methods involve a number of steps, many of which are performed in other extraction procedures. However, when the steps were compiled as described in the various aspects and embodiments presented in the specification the quality of the product produced by those steps was unexpected.

A detailed protocol is provided below. Cadaveric knees from the desired species are obtained. If obtained frozen, they are thawed before harvesting the desired tissues. The knees are prepared with solutions to reduce the bacterial load on the skin and then the skin is incised, and the underlying layers split until the desired tissue is reached. The tissue is harvested and placed into sterile containers. At this point, the tissue may be frozen at −20 or −80 degrees C. and stored for up to one year. Alternatively, the tissue can by lyophilized immediately.

After lyophilization, the tissue is homogenized using a blender, homogenizer, food processor, scalpel or some combination of these devices. An alternate device for cutting tissue can also be used. The small pieces of tissue are placed into a sterile salt solution which may contain antibiotics and/or an antimycotic. In one embodiment, the homogenization may be carried out at room temperature. In another embodiment, the homogenization may be carried out below room temperature. In another embodiment, the homogenization may be carried out at 4 degrees C. In another embodiment, the homogenization may be carried out below 4 degrees C. In one embodiment, dry ice is used to maintain the desired temperature of the tissue. In another embodiment, the homogenizing instrument is cooled to maintain the desired temperature. In another embodiment, the homogenizing vessel is cooled to maintain the desired temperature. In another embodiment, all parts of the homogenizing elements are sterilizable. In another embodiment, all instrumentation which could potentially contact the tissue is sterilizable. In another embodiment, all instrumentation which could potentially contact the tissue is sterile. In another embodiment, all instrumentation which could potentially contact the tissue is substantially free of endotoxin.

A salt extraction may be used to treat the tissue. The homogenized tissue may be placed into a tube containing a salt solution at a given concentration. In one embodiment, the solution is a 10% salt solution. In another embodiment, the solution is a 20% salt solution. In another embodiment, the solution is a 30% salt solution. In another embodiment, the solution is a >30% salt solution. In another embodiment, the solution is a <10% salt solution. In one embodiment, the salt solution is NaCl (sodium chloride). In another embodiment, the salt solution is CaCl2, calcium chloride. The salt extraction step may be carried out at a specified temperature. In one embodiment, the salt extraction may be carried out at room temperature. In another embodiment, the salt extraction may be carried out below room temperature. In another embodiment, the salt extraction may be carried out at 4 degrees C. In another embodiment, the salt extraction may be carried out below 4 degrees C.

Treatment to remove cell and cell debris may be carried out. The materials used to remove the cell debris may consist of enzymes, chemicals, detergents, salt solutions or hyperosmotic solutions. A physical agent, such as ultrasonic agitation, ultrasound, mechanical agitation or electronic stimulation may be used as a decellularization agent. The agents used to remove the cells and cell debris may consist of synthetic or natural materials. The tissue may be exposed to these decellularization agents for a specific time period. In one embodiment, the time period is 1 hour. In another embodiment, the time period is 1 to 5 hours. In another embodiment, the time period is 5 to 10 hours. In another embodiment, the time period is 10 to 24 hours. In another embodiment, the time period is greater than 24 hours. In another embodiment, the time period is less than 1 hour. The tissue may be exposed to these decellularization agents at a specific temperature. In one embodiment, the decellularization process may be carried out at room temperature. In another embodiment, the decellularization process may be carried out below room temperature. In another embodiment, the decellularization process may be carried out at 4 degrees C. In another embodiment, the decellularization process may be carried out below 4 degrees C. The tissue may be washed after the decellularization process. This wash may be performed using water, saline or other diluents. In one embodiment, the decellularization agent is an enzyme. In another embodiment, the decellularization agent is sodium dodecyl sulfate (SDS). In another embodiment, the decellularization agent is DNAse. In another embodiment, the decellularization agent is RNAse. In another embodiment, the decellularization agent is Triton X. In another embodiment, the decellularization agent is hypertonic NaCl. In another embodiment, the decellularization agent is elastase. In another embodiment, the decellularization agent is trypsin. In another embodiment, the decellularization agent is a matrix metalloproteinase. A second salt extraction may be performed after the decellularization process. rinse step may be performed after the decellularization process or after the salt extraction.

A step involving use of a citrate buffer may be used. The citrate solution may be used to extract additional collagen. The citrate buffer may be used at a pH=4. The citrate buffer may be placed in contact with the tissue for as long as 48 hours. The citrate buffer step may be carried out at room temperature. The citrate buffer step may be carried out at 4 degrees C. The tissue may be rinsed after addition of the citrate to remove all or some of the citrate.

Ultracentrifugation may be used to process the tissue. Spin speeds of over 1000 rpm may be used to pellet the tissue. This step may be alternated and repeated with wash steps with sterile solutions of acid, base, or neutral solutions.

An additional enzyme step may be used to break the collagen and/or glycosaminoglycans down into smaller fragments. An embodiment of this enzyme step would use collagenase type I. An embodiment of this enzyme step would use collagenase type II. An embodiment of this enzyme step would use collagenase type III. An embodiment of this enzyme step would use a matrix metalloproteinase. An embodiment of this enzyme step would use matrix metalloproteinase-1. An embodiment of this enzyme step would use matrix metalloproteinase-13. An embodiment of this enzyme step would use pepsin. An embodiment of this enzyme step would use elastase. An embodiment of this enzyme step would use trypsin. An embodiment of this enzyme step would use an aggrecanase. An embodiment of this enzyme step would use chondroitinase.

A collagen extract as used herein refers to a high grade collagen slurry that is useful in preparing collagen based scaffolds or tissue scaffolds. The term collagen extract is used interchangeably herein with the terms slurry or collagen slurry. A collagen scaffold as used herein is a solid or semi-solid/liquid material useful for implantation into a human subject or animal subject to repair damaged tissue and/or to deliver compounds and/or cells to the subject. The term collagen scaffold is used interchangeably herein with the terms sponge or collagen sponge.

Detailed methods for preparing the collagen scaffold are provided below. The collagen slurry is prepared using the steps above. The collagen content of the slurry is checked using the SIRCOL assay or similar assay for collagen content. The slurry is then lyophilized to remove all water and then resuspended with a measured amount of water, saline or other diluent to result in a slurry with the desired concentration of collagen. A strong acid or base can be added to the slurry to bring the pH to a desired level to inactivate any enzymes or chemicals used in the processing of the slurry that are desired to be inactivated before implantation. Additional acid or base, or a buffer with a pK between 7 and 8, can be then used to bring the pH of the solution to the desired range for implantation or combination with cells or proteins. The osmolarity of the slurry can be adjusted to the desired range using a salt solution, or an acid or base. Once the slurry has the appropriate pH and osmolarity, it can be subjected to heat or cold to cause self-assembly or gelation of the collagen. After gelation, lyophilization of the scaffold can be used to produce a scaffold, sponge or powder. Alternatively, the solution can be maintained as a gel. In an embodiment, conditions are maintained to prevent collagen self-assembly until after implantation of the collagen material into the joint.

Thus, in some aspects, the invention involves a method for making a collagen scaffold. At its most basic the method involves steps of preparing a neutralized collagen slurry, heating the neutralized collagen slurry and freeze drying the heated neutralized collagen slurry. Preparing a neutralized collagen slurry can be achieved by mixing a collagen slurry with a neutralizing buffer. It may also involve adding a calcium containing solution. The heating step may be performed, for instance in a mold in a dry oven or in an incubator.

The methods of preparing a collagen extract involve preparing ground tissue by grinding freeze dried collagenous tissue that has been isolated from a mammal. This can be performed by a homogenizer or similar device. A similar device is one that is useful for breaking the tissue into small pieces that can be effectively extracted. The methods also involve performing a first salt extraction on the ground tissue to produce a salt extracted collagen, treating the salt extracted collagen with a detergent solution, followed by an enzyme (in some embodiments elastase, in some embodiments RNase and/or Dnase, in some embodiments trypsin, papain or one or more collagenase solutions) digestion and EDTA incubation to produce a collagen mixture, performing a second salt extraction on the collagen mixture and centrifuging the salt extracted mixture to produce a pellet, incubating the pellet with a citrate buffer, followed by acid solubilization and pepsin digestion.

The collagen scaffolds described herein may be used alone or in combination with three-dimensional (3-D) scaffolds or other traditional repair devices. The material provides a connection between the ruptured ends of the ligament and fibers, or provides a replacement for a torn ligament, after injury, and encourages the migration of appropriate healing cells to form scar and new tissue and thus facilitating healing and regeneration.

It is intended that the use of the compositions and methods of the present invention involve the repair, replacement, reconstruction or augmentation of specific tissue types. Articular injuries include both intra-articular and extra-articular injuries. Intra-articular injuries involve, for instance, injuries to meniscus, ligament and cartilage. Extra-articular injuries include, but are not limited to injuries to the ligament, tendon or muscle. Thus, the methods of the invention may be used to treat injuries to the Anterior cruciate ligament (ACL), Lateral collateral ligament (LCL), Posterior cruciate ligament (PCL), Medial collateral ligament (MCL), Volar radiocarpal ligament, Dorsal radiocarpal ligament, Ulnar collateral ligament, Radial collateral ligament, meniscus, labrum, for example glenoid labrum and acetabular labrum, cartilage, for example, and other tissues exposed to synovial fluid after injury.

The injury being treated may be, for instance, a torn or ruptured ligament. A ligament is a short band of tough fibrous connective tissue composed of collagen fibers. Ligaments connect bones to other bones to form a joint. A torn ligament is one where the ligament remains connected but has been damaged causing a tear in the ligament. The tear may be of any length or shape. A ruptured ligament is one where the ligament has been completely severed providing two separate ends of the ligament. A ruptured ligament may provide two ligament ends of similar or different lengths. The rupture may be such that a ligament stump is formed at one end.

An example of a ruptured anterior cruciate ligament is described for exemplary purposes only. The anterior cruciate ligament (ACL) is one of four strong ligaments that connects the bones of the knee joint. The function of the ACL is to provide stability to the knee and minimize stress across the knee joint. It restrains excessive forward movement of the lower leg bone, the tibia, in relation to the thigh bone, the femur, and limits the rotational movements of the knee. An anterior cruciate ligament is ruptured such that it no longer forms a connection between the femur bone and the tibia bone. The resulting ends of the ruptured ACL may be of any length. The ends may be of a similar length, or one end may be longer in length than the other.

The damaged or injured tissue is treated with the collagen scaffolds described herein which is typically a sterile solution of solubilized collagen. Solubilized collagen, as used herein, is enzyme solubilized collagen including one or more of Type I, II, III, IV, V, X collagen. Preferably the enzyme solubilized collagen is tropocollagen or Atelocollagen rather than fibrillar collagen in order to reduce the antigenicity of the material. The collagen is isolated from a tissue source and mechanically minced and extracted as described above. Preferably the collagen is kept cold (4 deg C or on ice) during storage and throughout parts of the preparation.

In one embodiment the solubilized collagen is Type I collagen. As used herein the term, "Type I collagen" is characterized by two $\alpha 1(I)$ chains, and one $\alpha\ 2(I)$ chains (heterotrimeric collagen). The $\alpha 1$ (I) chains are approximately 300 nm long. Type I collagen is predominantly found in bone, skin (in sheet-like structures), and tendon (in rope-like structures). Type I collagen is further typified by its reaction with the protein core of another connective tissue component known as a proteoglycan. Type I collagen contains signaling regions that facilitate cell migration.

Natural sources of collagen may be obtained from animal or human sources. For instance, it may be derived from rat, pig, cow, or human tissue or tissue from any other species. Tendons, ligaments, muscle, fascia, skin, cartilage, tail, or any source of collagenous tissue are useful. The material is then implanted into a subject of the same or different species. The terms "xenogeneic" and "xenograft" refer to cells or tissue which originates with or is derived from a species other than that of the recipient. Alternatively, the collagen may be obtained from autologous cells. For instance, the collagen may be derived from a patient's fibroblasts which have been cultured. The collagen may then be used in that patient or other patients. The terms "autologous" and "autograft" refer to tissue or cells which originate with or are derived from the recipient, whereas the terms "allogeneic" and "allograft" refer to cells and tissue which originate with or are derived from a donor of the same species as the recipient. The collagen may be isolated any time before surgery.

The collagen scaffold may be in a concentration of 1-100 mg/ml in the solution. Such high concentrations of collagen are useful for producing viscosity levels that are desirable for the methods of the invention. Most commercially available collagen solutions are of lower concentrations. Higher concentrations can be made, for instance, using the methods described herein. In other embodiments the solubilized collagen solution has a concentration of 1 mg/ml to less than 5 mg/ml.

The collagen scaffold is sterile for in vivo use. The solution may be sterilized and/or components of the solution may be isolated under sterile conditions using sterile techniques to produce a sterile composition. The final desired properties of the composition may be determinative of how the solution is sterilized because some sterilization techniques may affect properties such as viscosity. If certain components of the solution are not to be sterilized, i.e., the collagen isolated from natural sources, the remaining components can be combined and sterilized before addition of the collagen, or each component can be sterilized separately. The solution can then be made by mixing each of the sterilized components with the collagen that has been isolated using sterile techniques under sterile conditions. Sterilization may be accomplished, for instance, by autoclaving at temperatures on the order of about 115° C. to 130° C., preferably about 120° C. to 125° C. for about 30 minutes to 1 hour. Gamma radiation is another method for sterilizing components. Filtration is also possible, as is sterilization with ethylene oxide. Some embodiments include sterilization under low temperature conditions.

The collagen materials described herein may contain additional components, such as insoluble collagen, other extracellular matrix proteins (ECM), such as proteoglycans and glycosaminoglycans, fibronectin, laminin, entectin, decorin, lysyl oxidase, crosslinking precursors (reducible and non-reducible), elastin, elastin crosslink precursors, cell components such as, cell membrane proteins, mitochondrial proteins, nuclear proteins, cytosomal proteins, and cell surface receptors, growth Factors, such as, PDGF, TGF, EGF, and VEGF, and hydroxyproline.

The methods described above include the addition of one or more buffers or solutions to produce the collagen extract and scaffold. The following buffers and solutions are useful in the methods of the invention:

Tris buffer pH=7.5:
Tris$_{MW}$=121.14 and for 0.05M we'll need 6.057 g per liter of ultra pure water (Milli-Q)
Add approx. 6.1 g of Tris in 800 ml of ultra pure water;
Stir at RT until dissolved;
pH to approx. 7.5 using HCl. Around 4 ml of 37% (~12N) HCL; Add 3 ml and then add drop by drop with pH meter in until 7.5 is reached
Complete to 1 liter with ultra pure water;
NaCl solution:
20% is equivalent to 1.71M of NaCl solution (NaCl$_{MW}$=58.44)
Add 20 g of NaCl per 100 ml of Tris buffer;
Stir at RT until dissolved;
Filter.
Thrombin solution:
1. Company: MP Biomwdicals
Tel: 800-883-9323
Cat #: 08820361
Lot #: 4869E
Quantity: 10×1 k unit
1,000 unit (1 vial) dilute in 40 mM CaCl2, depends on the concentration of thrombin.
Preparation of L-ascorbic acid phosphate magnesium salt n-hydrate solution:
Company: Wako
Cat #: 013-12061
MW=289.54
Stock solution: 0.5 g in 50 ml of plain DMEM, dissolve, filter, aliquot 1.5 ml.
1.5 ml aliquot in 500 ml DMEM,
Final concentration: 103.6 μM.
Literature: 100 μM to 250 μM.
Preparation of MMP-3 Solution (collagenase):
Concentration of 40.1 μg/ml needed, sold in concentration of 260 mg/ml (Chemicon #CC0315),
Use 0.001 ml of 260 mg/ml solution and add 249.999 ml of PBS.
Preparation of MMP-1 Solution (collagenase):
Concentration of 1.12 μg/ml, sold in concentration of 0.52 mg/ml (Chemicon #CC1031),
Use 19.27 ml of 0.52 mg/ml solution and add 230.73 ml of PBS.
Preparation of RNAse/DNAse solution:
Add 476 mg MgCl$_2$ to 50 ml PBS and stir until dissolved,
Add DNAse and RNAse into 5 ml tube and dissolve in MgCl PBS solution, pour into MgCl PBS bottle, rinse out multiple times, stir until dissolved.
Preparation of MMP-2/MMP-9 Solution (Collagenase):
Concentration of 17.0 ug/ml, sold in concentration of 0.10 mg/ml (Chemicon #CC071),
Use 42.50 ml of 0.10 mg/ml solution and add 207.5 ml of PBS to make 250 ml solution.
Preparation of Elastase Solution:
Concentration of 3.50 μg/ml, sold in 5 mg unit (Worthington #55K8226),
Dissolve 0.875 mg of Elastase in 250 ml of PBS.
Preparation of Papain Digest Solution:
Papain Digest buffer (100 mM sodium phosphate buffer/10 mM Na$_2$EDTA/10 mM $_L$-cysteine/0.125 mg/mL papain) Prepare under laminar flow hood. Cysteine and papain enzyme are unstable; use fresh.
  a. Prepare 40 mL PBE-10 mM cysteine; combine 40 mL PBE buffer with 63.0 mg L-cysteine hydrochloride. Filter sterilize with a 0.22-μm syringe filter.
  b. Prepare 20 mL papain digest buffer: transfer 20 mL sterile PBE-cysteine to a fresh conical tube. Add papain enzyme using sterile technique. Swipe rubber stopper of the papain solution with ethanol, swirl to resuspend, and remove papain solution with sterile 1-mL syringe and hypodermic needle to a sterile eppendorf tube. Use a pipetteman to as 2.5 mg papain enzyme to 20 mL PBE-cysteine (add 1004 if papain is 25 mg/mL).
Add papain digest to gel, place tubes in heat block at 60° C. until digested (>4 hours).
EDTA solution
Add 20 mg EDTA to 100 ml PBS and stir until dissolved.
Citrate buffer pH=4.0: Citric Acid-Sodium Citrate Buffer Solutions, pH 3.0-6.2: Citric acid monohydrate, C$_6$H$_8$O$_7$·H$_2$O, M. wt. 210.14; 0.1M-solution contains 21.01 g/l. Trisodium citrate dihydrate, C$_6$H$_8$O$_7$Na$_3$·2H$_2$O, M. wt. 294.12; 0.1M-solution contains 29.41 g/l.

| pH | x ml 0.1M-citric acid | y ml 0.1M-trisodium |
| --- | --- | --- |
| 3.0 | 82.0 | 18.0 |
| 3.2 | 77.5 | 22.5 |
| 3.4 | 73.0 | 27.0 |
| 3.6 | 68.5 | 31.5 |
| 3.8 | 63.5 | 36.5 |
| 4.0 | 59.0 | 41.0 |
| 4.2 | 54.0 | 46.0 |
| 4.4 | 49.5 | 50.5 |
| 4.6 | 44.5 | 55.5 |
| 4.8 | 40.0 | 60.0 |
| 5.0 | 35.0 | 65.0 |
| 5.2 | 30.5 | 69.5 |
| 5.4 | 25.5 | 74.5 |
| 5.6 | 21.0 | 79.0 |

| pH | x ml 0.1M-citric acid | y ml 0.1M-trisodium |
|---|---|---|
| 5.8 | 16.0 | 84.0 |
| 6.0 | 11.5 | 88.5 |
| 6.2 | 8.0 | 92.0 |

Buffers: NaOH is 1M, HEPES is 0.1M.

The above-described buffers and solutions are exemplary. The skilled artisan would recognize that some substitutions or adjustments could be made to the buffers and solutions.

The buffers and solutions also may or may not include an antibiotic. For instance, the antibiotic may be penicillin/streptomycin. Alternatively, it may be a clinical antibiotic, which is used in human patients for the treatment or prevention of diseases, such as any of those described in Remington's Pharmaceutical Sciences (Mack Publishing Co., Easton Pa.), which is hereby incorporated by reference.

The buffer may be a single component, or it may be multiple components added at the same time or different times. If the buffer is a single component it should have properties that enable it to produce a solution having a desirable pH range and osmolarity. In some instances, it is desirable to have at least two buffer components, a collagen buffer solution and a neutralizing buffer. The collagen buffer solution may be used to prepare the collagen in a solution. In some instances, the prepared collagen solution may be stored for extended periods of time.

In certain embodiments, the collagen solution is mixed with cells such as platelets or white blood cells or red blood cells or stem cells or fibroblasts. In some embodiments, the cells are derived from the subject to be treated. In other embodiments, the cells are derived from a donor that is allogeneic to the subject.

In certain embodiments, platelets may be obtained as platelet rich plasma (PRP). This component contains fibrin and platelets as well as other plasma proteins found in the blood. There may also be some white blood cells (WBC) and red blood cells (RBC) found in this preparation. Preferably the platelet concentration of PRP is at least 100 K/ml, and preferably over 300 K/ml. For instance, the platelet concentration may be at least 1× what it is in the blood of the patient, and preferably 1.5× or greater In order to maintain the stability of the cells a physiologic pH (i.e., 6.2 to 7.6) and a physiologic plasma osmolarity (i.e., 280-360 osms/kg) is used. In order to enhance the function of the PRP, preferably the PRP is used within 7 days of being drawn from the patient or donor. Often the PRP is isolated from the patient at time of surgery. Preferably it is stored at 20 to 37 deg C (room temp to body temp). However, isolation and storage of the cells may be achieved by any methods and for any length of time known in the art for maintaining the activity of the active components.

In a non-limiting example, platelets may be isolated from a subject's blood using techniques known to those of ordinary skill in the art. As an example, a blood sample may be drawn into a tube containing an anticoagulant, and the subsequent solution centrifuged at 700 rpm for 20 minutes and the platelet-rich plasma upper layer removed. Platelet density may be determined using a cell count as known to those of ordinary skill in the art. The platelet rich plasma may be mixed with collagen and applied to the patient.

In a non-limiting example, white blood cells may also be isolated from a subject's blood using techniques known to those of ordinary skill in the art. As an example, a blood sample may be drawn into a tube containing an anticoagulant and centrifuged at 700 rpm for 20 minutes and the buffy coat containing white blood cells removed. WBC density may be determined using a cell count as known to those of ordinary skill in the art. The WBCs can be mixed with collagen and applied to the patient. The collagen solution may also include any one or more of an anti-plasmin agent, an extracellular matrix (ECM) protein, other protein or enzyme inhibitors, antibodies to plasmin, antibodies to tissue plasminogen activator or urokinase plasminogen activator, non-toxic crosslinkers, calcium, dextrose or other sugars and cell nutrients in physiological concentrations. Anti-plasmin agents include but are not limited to antifibrinolytic enzymes such as plasminogen inactivator, plasminogen binding $\alpha_2$ antiplasmin, non-plasminogen binding $\alpha_2$ antiplasmin, $\alpha_2$ macroglobulin, $\alpha_2$ plasmin inhibitor, $\alpha_2$ antiplasmin, and thrombin activatable fibrinolysis inhibitor. Other protein or enzyme inhibitors include but are not limited to anti-enzymatic proteins including inhibitors of collagenase, trypsin, matrix metalloproteinases, elastase and hyaluronidase. The ECM is composed of fibrillar and non-fibrillar components. The major fibrillar proteins are collagen and elastin. The ECM includes for instance, diverse combinations of collagens, fibrinogen, proteoglycans, elastin, hyaluronic acid, and various glycoproteins including laminin, fibronectin, heparan sulfate proteoglycan, and entactin. Non-toxic crosslinkers include but are not limited to tissue transglutaminases, lysyl oxidase, fibrin, fibronectin, and reducible and non-reducible crosslink precursor molecules.

The collagen solution, with or without any of the above-described additional components, may be stored as a liquid or gel material or may be dried and stored as a powder. For instance, a collagen solution may be lyophilized to produce a powder. The powder may then be reconstituted in a buffer solution. Neutralizing agent may be present in the reconstitution buffer or may be added as a separate buffer or as salts.

The final collagen solution includes collagen, buffer and cells, such as PRP or WBCs. The components are mixed on a microscopic level, rather than layered. Preferably it has a pH of 7.4 and a minimum viscosity of approximately 1,000 centipoise. Preferably the viscosity is in the range of 1,000-200,000 centipoise.

While the degree of "solidness" may vary from application to application, generally speaking collagen solutions of the present invention will exhibit viscosities in the full range of from liquid to gel-like to solid-like or even powder form. A collagen solution having optimal viscosity can be obtained directly from the source of collagen, depending on the concentration of the collagen. However, a collagen solution not having an optimal viscosity can be manipulated to create the correct viscosity. The viscosity of a collagen solution may be lowered by diluting the solution. The viscosity of a lower viscosity collagen solution may be increased to increase gelation. One method to do this is to lyophilize the collagen solution and rehydrate it in a specific amount of water. Another method to do this is to stop the lyophilization process before it is completed, thus only removing part of the water from the gel and concentrating the collagen. Gelation is the change in viscosity from a fluid-like composition to a solid or gel-like composition. Gelation or viscosity of a solution may also be increased by adding one or more of the following: other ECM molecules, including but not limited to, insoluble collagen, fibrin, fibronectin, and cellulose; cell additions, including but not limited to, platelets and fibroblasts; non-toxic crosslinking agents, including but not limited to, tissue transglutaminases, lysyl oxidase, fibrin, and fibronectin; and other high viscosity materials with low osmolarity, including but not limited to, alginate and synthetic filler materials.

The term "repair material" as used herein refers to the final formulation of collagen solution with cells to be delivered to the subject.

The collagen solution or repair material may include additional materials, such as growth factors, antibiotics, insoluble or soluble collagen, a cross-linking agent, thrombin, stem cells, a genetically altered fibroblast, platelets, water, plasma, extracellular proteins and a cell media supplement. Alternatively, the collagen solution or repair material may exclude any of these components, and in particular thrombin. The additional materials may be added to affect cell proliferation, extracellular matrix production, consistency, inhibition of disease or infection, tonicity, cell nutrients until nutritional pathways are formed, and pH of the collagen solution or repair material. All or a portion of these additional materials may be mixed with the collagen solution or repair material before or during implantation, or alternatively, the additional materials may be implanted proximate to the defect area after the repair material is in place.

The repair material of the invention may be applied directly to the tissue alone or it may be used in combination with a tissue healing device such as a scaffold. A device or scaffold may be any shape that is useful for implantation into a subject. The scaffold, for instance, can be tubular, semi-tubular, cylindrical, including either a solid cylinder or a cylinder having hollow cavities, a tube, a flat sheet rolled into a tube so as to define a hollow cavity, liquid, an amorphous shape which conforms to that of the repair space, a "Chinese finger trap" design, a trough shape, or square. Other shapes suitable for the scaffold of the device as known to those of ordinary skill in the art are also contemplated in the invention.

The scaffold may be pretreated with the repair material prior to implantation into a subject. For instance, the scaffold may be soaked in a repair material prior to or during implantation into a repair site. The repair material may be injected directly into the scaffold prior to or during implantation. The repair material may be injected within a tubular scaffold at the time of repair.

In aspects of the invention, a device for use with the repair material of the invention for repairing a damaged tissue includes a scaffold and/or an anchor. A scaffold is capable of insertion into a repair site and either forming a connection between the ends of a ruptured tissue, or forming around a torn tissue such that, in either case, the integrity and structure of the tissue is maintained. A scaffold is preferably made of a compressible, resilient material which has some resistance to degradation by synovial fluid. Synovial fluid as part of normal joint activity, naturally prevents clot formation. This fibrinolytic process would result in the premature degradation of the scaffold and disrupt the healing process of the tissue. The material may be natural or synthetic and may be either permanent or biodegradable material, such as polymers and copolymers. The scaffold can be composed, for example, of collagen fibers, collagen gel, foamed rubber, natural material, synthetic materials such as rubber, silicone and plastic, ground and compacted material, perforated material, or a compressible solid material.

A scaffold that is capable of compression and expansion is particularly desirable. For example, a sponge scaffold may be compressed prior to or during implantation into a repair site. A compressed sponge scaffold allows for the sponge scaffold to expand within the repair site. Examples of scaffolds useful according to the invention are found in U.S. Pat. No. 6,964,685 and US Patent Application Nos. 2004/0059416 and 2005/0261736, the entire contents of each are herein incorporated by reference.

A scaffold may be a solid material such that its shape is maintained, or a semi-solid material capable of altering its shape and or size. A scaffold may be made of expandable material allowing it to contract or expand as required. The material can be capable of absorbing plasma, blood, other body fluids, liquid, hydrogel, or other material the scaffold either comes into contact with or is added to the scaffold.

A scaffold material may incorporate therapeutic proteins including, but not limited to, hormones, cytokines, growth factors, clotting factors, anti-protease proteins (e.g., alpha1-antitrypsin), angiogenic proteins (e.g., vascular endothelial growth factor, fibroblast growth factors), antiangiogenic proteins (e.g., endostatin, angiostatin), and other proteins that are present in the blood, bone morphogenic proteins (BMPs), osteoinductive factor (IFO), fibronectin (FN), endothelial cell growth factor (ECGF), cementum attachment extracts (CAE), ketanserin, human growth hormone (HGH), animal growth hormones, epidermal growth factor (EGF), interleukin-1 (IL-1), human alpha thrombin, transforming growth factor (TGF-beta), insulin-like growth factor (IGF-1), platelet derived growth factors (PDGF), fibroblast growth factors (FGF, bFGF, etc.), and periodontal ligament chemotactic factor (PDLGF), for therapeutic purposes. A lyophilized material is one that is capable of swelling when liquid, gel or other fluid is added or comes into contact with it.

A device for implantation may also include one or more anchors. An anchor is a device capable of insertion into a bone or tissue such that it forms a stable attachment to the bone or tissue. In some instances, the anchor is capable of being removed from the bone if desired. An anchor may be conical shaped having a sharpened tip at one end and a body having a longitudinal axis. The body of an anchor may increase in diameter along its longitudinal axis. The body of an anchor may include grooves suitable for screwing the anchor into position. An anchor may include an eyelet at the base of the anchor body through which one or more sutures may be passed. The eyelet may be oval or round and may be of any size suitable to allow one or more sutures to pass through and be held within the eyelet.

An anchor may be attached to a bone or tissue by physical or mechanical methods as known to those of ordinary skill in the art. An anchor includes, but is not limited to, a screw, a barb, a helical anchor, a staple, a clip, a snap, a rivet, or a crimp-type anchor. The body of an anchor may be varied in length. Examples of anchors, include but are not limited to, IN-FAST™ Bone Screw System (Influence, Inc., San Francisco, Calif.), IN-TAC™ Bone Anchor System (Influence, Inc., San Francisco, Calif.), Model 3000 AXYALOOP™ Titanium Bone Anchor (Axya Medical Inc., Beverly, Mass.), OPUS MAGNUM® Anchor with Inserter (Opus Medical, Inc., San Juan Capistrano, Calif.), ANCHRONTM, HEXALON™ TRINION™ (all available from Inion Inc., Oklahoma City, Okla.) and TwinFix AB absorbable suture anchor (Smith & Nephew, Inc., Andover, Mass.). Anchors are available commercially from manufacturers such as Influence, Inc., San Francisco, Calif., Axya Medical Inc., Beverly, Mass., Opus Medical, Inc., San Juan Capistrano, Calif., Inion Inc., Oklahoma City, Okla., and Smith & Nephew, Inc., Andover, Mass.

An anchor may be composed of a non-degradable material, such as metal, for example titanium 316 LVM stainless steel, CoCrMo alloy, or Nitinol alloy, or plastic. An anchor is preferably bioabsorbable such that the subject is capable of breaking down the anchor and absorbing it. Examples of bioabsorbable material include, but are not limited to, MONOCRYL (poliglecaprone 25), PDS II (polydioxanone), surgical gut suture (SGS), gut, coated VICRYL (polyglactin 910, polyglactin 910 braided), human autograft tendon material, collagen fiber, POLYSORB, poly-L-lactic acid (PLLA), polylactic acid (PLA), polysulfone, polylactides (Pla), racemic form of polylactide (D,L-Pla), poly(L-lactide-co-D,L-lactide), 70/30 poly(L-lactide-co-D,L-lactide), polyglycolides (PGa), polyglycolic acid (PGA), polycaprolactone (PCL), polydioxanone (PDS), polyhydroxyacids, and resorbable plate material (see e.g. Orthopedics, October 2002, Vol. 25, No. 10/Supp.). The anchor may be bioabsorbed over a period of time which includes, but is not limited to, days, weeks, months or years.

The scaffold may also be secured in place using sutures passed through bone tunnels or both and anchored on the outer surfaces of the bone using a button or small plate. Examples of these buttons are common shirt buttons or buttons made specifically for medical applications, for example the ENDOBUTTON (Smith and Nephew, Andover Mass.). In one embodiment, sutures are passed through bone tunnels in both femur and tibia, creating a suture stent to secure the scaffold in the knee.

A suture is preferably bioabsorbable, such that the subject is capable of breaking down the suture and absorbing it, and synthetic such that the suture may not be from a natural source. Examples of sutures include, but are not limited to, VICRYL™ polyglactin 910, PANACRYL™ absorbable suture, PDS® polydioxanone suture and PROLENE® polypropylene suture. Sutures are available commercially from manufacturers such as MITEK PRODUCTS division of ETHICON, INC. of Westwood, Mass. Alternatively, the suture is non-absorbable and is considered a permanent implant. In another embodiment, the suture is non-absorbable and is able to be released at a specific time point. Examples of non-absorbable sutures include ETHIBOND® EXCEL polyester suture, stainless steel wire or Teflon or nylon materials.

A staple is a type of anchor having two arms that are capable of insertion into a bone or tissue. In some instances, the arms of the staple fold in on themselves when attached to a bone or in some instances when attached to other tissue. A staple may be composed of metal, for example titanium or stainless steel, plastic, or any biodegradable material. A staple includes but is not limited to linear staples, circular staples, curved staples or straight staples. Staples are available commercially from manufacturers such as Johnson & Johnson Health Care Systems, Inc. Piscataway, N.J., and Ethicon, Inc., Somerville, N.J. A staple may be attached using any staple device known to those of ordinary skill in the art, for example, a hammer and staple setter (staple holder).

The device may be inserted into a repair site of the ruptured or torn tissue. A repair site is the area around a ruptured or torn tissue into which the material of the invention may be inserted. A device may be placed into a repair site area during surgery using techniques known to those of ordinary skill in the art. If a scaffold is used in the methods, the scaffold can either fill the repair site or partially fill the repair site. A scaffold can partially fill the repair site when inserted and expand to fill the repair site in the presence of blood, plasma anticoagulated blood, anticoagulated blood products or other fluids either present within the repair site or added into the repair site, such as the repair material.

The scaffold may be positioned in combination with a surgical technique. For instance, a hole may be drilled into a bone at or near a repair site of a ruptured or torn tissue and the scaffold attached by a suture through the hole to the bone. A bone at or near a repair site is one that is within close proximity to the repair site and can be utilized using the methods and devices of the invention. For example, a bone at or near a repair site of a torn anterior cruciate ligament is a femur bone and/or a tibia bone. A hole can be drilled into a bone using a device such as a Kirschner wire (for example a small Kirschner wire) and drill, or microfracture pics or awls.

A hole may be drilled into a bone on the opposite side to the repair site. A suture may be passed through the hole in the bone and attached to the bone. A scaffold is attached to the suture to secure the scaffold between the bone and an end of a ruptured tissue. A ruptured tissue provides two ends of the tissue that were previously connected. A scaffold may be attached to one or both ends of a ruptured tissue by one or more sutures. A suture may be attached to a second bone site at or near the repair site. The suture may be attached to the second bone using a second anchor.

In a typical arthroscopic procedure, for instance of the ACL, the surgeon prepares the patient for surgery by insufflating the patient's knee with sterile saline solution. Several cannulas are inserted into the knee and used as entry portals into the interior of the knee. A conventional arthroscope is inserted through one of the cannulas so that the knee may be viewed by the surgeon remotely.

In surgical reconstruction of a tissue such as ACL the surgeon may drill a tibial tunnel and a femoral tunnel in accordance with conventional surgical techniques using conventional surgical drills and drill guides. A replacement anterior cruciate ligament graft is then prepared and mounted in the tibial and femoral tunnels and secured using conventional techniques and known devices in order to complete the knee reconstruction.

The repair material may also be used in combination with a graft, such as an ACL graft. Several types of ACL grafts are available for use by the surgeon in ACL reconstruction. The grafts may be autografts that are harvested from the patient, for example patellar bone-tendon-bone grafts, or hamstring grafts. Alternatively, the grafts can be xenografts, allografts, or synthetic polymer grafts. Allografts include ligamentous tissue harvested from cadavers and appropriately treated and disinfected, and preferably sterilized. Xenografts include harvested connective tissue from animal sources such as, for example, porcine tissue. Typically, the xenografts must be appropriately treated to eliminate or minimize an immune response. Synthetic grafts include grafts made from synthetic polymers such as polyurethane, polyethylene, polyester and other conventional biocompatible bioabsorbable or nonabsorbable polymers and composites, such as the scaffolds described herein.

The repair material is applied to a subject. The application to the subject involves surgical procedures. The following is an example of a surgical procedure which may be performed using the methods of the invention. The affected extremity is prepared and draped in the standard sterile fashion. A tourniquet may be used if indicated. The intra-articular lesion is identified and defined, the tissue ends are pretreated, either mechanically or chemically, and if a scaffold is being used, the scaffold is introduced into the tissue defect. If the scaffold has not been pre-soaked in any additional components designed to facilitate repair, for example platelets, growth factors or other cells, or if more repair material is desired, then the repair material is added to the scaffold. The scaffold may be reinforced by placement of sutures or clips. If no scaffold is used the tissue defect is coated directly with repair material. The post-operative rehabilitation is dependent on the joint affected, the type and size of lesion treated, and the tissue involved.

The methods of the invention may be achieved using arthroscopic procedures. Standard arthroscopy equipment may be used. Initially, diagnostic arthroscopy may be performed to identify the appropriate repair site. If a scaffold is used it should be compressible to allow introduction through arthroscopic portals, incisions and equipment. The repair material can be placed in the repair site by direct injection. After the procedure the arthroscopic portals can be closed, and a sterile dressing placed.

A subject includes, but is not limited to, any mammal, such as human, non-human primate, mouse, rat, dog, cat, horse or cow. In certain embodiments, a subject is a human.

The materials used in the invention are preferably biocompatible, pharmaceutically acceptable and sterile. As used herein, the term "biocompatible" refers to compositions (e.g. cells, tissues, matrices, etc.) that do not substantially disrupt the normal biological functions of other compositions to which they contact. In selected embodiments, the present invention also contemplates biocompatible materials that are both biodegradable and non-biodegradable.

As described above, each of the components of the repair material may be prepared sterilely. If, however, one or more components is not retrieved or processed in a sterile manner then it can be sterilized prior to application to the subject. For instance, the material (preferably without the cells) may be sterilized after production using gamma irradiation, ethanol, autoclave sterilization or other known sterilization methods.

As used herein, the term "pharmaceutically acceptable" means a non-toxic material that does not interfere with the effectiveness of the biological activity of the scaffold material or repair material. The term "physiologically acceptable" refers to a non-toxic material that is compatible with a biological system such as a cell, cell culture, tissue, or organism. The characteristics of the carrier will depend on the route of administration. Physiologically and pharmaceutically acceptable carriers include diluents, fillers, salts, buffers, stabilizers, solubilizers, and other materials which are well known in the art. The term "carrier" denotes an organic or inorganic ingredient, natural or synthetic, with which the scaffold material is combined to facilitate the application. The components of the pharmaceutical compositions also are capable of being co-mingled with the device of the present invention, and with each other, in a manner such that there is no interaction which would substantially impair the desired pharmaceutical efficacy.

In some embodiments the repair material composition is injectable. Injectable compositions may contain formulatory agents such as suspending, stabilizing and/or dispersing agents. Pharmaceutical formulations for injection may contain substances which increase the viscosity of the suspension, such as sodium carboxymethyl cellulose, sorbitol, or dextran. Optionally, the materials may also contain suitable stabilizers.

The collagen solution may be in the form of a liquid, gel or solid, prior to addition of the cells. Once the cells are added, the repair material will begin to increase in gelation for application to the body. If the collagen solution is a liquid or gel the cells may be directly added to the solution.

Alternatively, the collagen solution may be in powder form for constitution with a suitable vehicle, e.g., sterile pyrogen-free water, before use. Neutralization agent may be added before or after reconstitution. After the powder is reconstituted it is mixed with cells to form the repair material.

As used herein, the term "gel" refers to the state of matter between liquid and solid. As such, a "gel" has some of the properties of a liquid (i.e., the shape is resilient and deformable) and some of the properties of a solid (i.e., the shape is discrete enough to maintain three dimensions on a two-dimensional surface.). A gel may be provided in pharmaceutical acceptable carriers known to those skilled in the art, such as saline or phosphate buffered saline. Such carriers may routinely contain pharmaceutically acceptable concentrations of salt, buffering agents, preservatives, compatible carriers and optionally other therapeutic agents.

An example of a gel is a hydrogel. A hydrogel is a substance that is formed when an organic polymer (natural or synthetic) is crosslinked via covalent, ionic, or hydrogen bonds to create a three-dimensional open-lattice structure which entraps water molecules to form a gel. A polymer may be crosslinked to form a hydrogel either before or after implantation into a subject. For instance, a hydrogel may be formed in situ, for example, at the repair site. In certain embodiments, the repair material forms a hydrogel within the repair site upon exposure to body temperatures.

The repair material, including the collagen solution and the cells will begin to set once it is created. The setting process can be delayed by maintaining cold temperatures or it may be accelerated by warming the mixture. In certain embodiments, a quick set composition of the repair material is provided. The quick set composition is capable of forming a set scaffold within 10 minutes of mixture when the material is exposed to temperatures of greater than 30° C. In some embodiments formation of the scaffold takes approximately 5 minutes at such temperatures. The quick set composition is achieved by preparing the collagen solution at concentrations and viscosities as described herein. The quick set nature can be further enhanced by the addition of non-toxic cross linking agents. Such compositions should be applied quickly to the tissue defect to sufficiently set before closure of the defect and surgery area.

The invention also includes in some aspects kits for making the collagen material. A kit may include one or more containers housing the components of the invention. The kit may be designed to facilitate use of the methods described herein and can take many forms. Each of the compositions of the kit, where applicable, may be provided in liquid form (e.g., in solution), or in solid form, (e.g., a dry powder). In certain cases, some of the compositions may be constitutable or otherwise processable (e.g., to an active form), for example, by the addition of a suitable solvent or other species (for example, water or a cell culture medium), which may or may not be provided with the kit. As used herein, "instructions" can define a component of instruction and/or promotion, and typically involve written instructions on or associated with packaging of the invention. Instructions also can include any oral or electronic instructions provided in any manner such that a user will clearly recognize that the instructions are to be associated with the kit, for example, audiovisual (e.g., videotape, DVD, etc.), Internet, and/or web-based communications, etc. The written instructions may be in a form prescribed by a governmental agency regulating the manufacture, use or sale of pharmaceuticals or biological products, which instructions can also reflect approval by the agency of manufacture, use or sale for human administration.

The kit may contain any one or more of the components described herein in one or more containers. As an example, in one embodiment, the kit may include instructions for mixing one or more components of the kit. The kit may include a container housing the collagen source. The collagen may be in the form of a liquid, gel or solid (powder). The collagen may be prepared sterilely, packaged in syringe and shipped refrigerated. Alternatively, it may be housed in a vial or other container for storage. A second container may have buffer solution premixed prepared sterilely or in the form of salts.

The kit may be sterilized after the accessories are added, thereby allowing the individual accessories in the container to be otherwise unwrapped. The kits can be sterilized using any appropriate sterilization techniques, such as radiation sterilization, heat sterilization, or other sterilization methods known in the art.

The kit may include disposable components supplied sterile in disposable packaging. The kit may also include other components, depending on the specific application, for example, containers, cell media, salts, buffers, reagents, syringes, needles, etc.

In another example, a collagen solution can be lyophilized first and then rehydrated. The collagen slurry thus produced can be neutralized by a method known in the art (e.g., using a HEPES buffer) and then incubated under suitable conditions to allow for gelation. The collagen gel thus formed can be lyophilized to produce a collagen sponge. Afterwards, the collagen sponge can be soaked in a calcium solution having a suitable calcium concentration (e.g., those described herein) for a suitable period and then lyophilized to produce a calcium-containing collagen material. In another embodiment, the structural member and the biomaterials described herein are substantially free of thrombin. In another embodiment, no non-autologous thrombin is added to the biomaterial before, during, or after implantation. In another embodiment, thrombin from any source is added to the biomaterial before, during, or after implantation. In another embodiment, the only thrombin that is added to the biomaterial before, during, or after implantation is that found in the autologous blood or plasma comprising the implanted or injected material.

In some embodiments, the biomaterial described herein (e.g., collagen materials or ECM scaffolds) are substantially free of one or more of the following cell components: nucleic acid (DNA and/or RNA), glycosaminoglycan (GAG), phospholipid, active pepsin, and active virus. Such compositions can be prepared by treating the biomaterial, the structural member contained therein, or the solution for preparing the biomaterial/structural member to remove DNA, DNA fragments, RNA and RNA fragments, cells, fragments of cell membrane, cell components, and/or to minimizes the incorporation of endotoxins. The biomaterials, structural members, and/or solutions for preparing such can also be treated to inactivate pepsin and remove/inactivate viruses. Such treatments can be performed following methods known in the art and/or those descried herein (see Examples 7 and 8 below).

In some embodiments, the composite of structural members and biomaterials described herein (e.g., collagen materials or ECM scaffolds and/or a bio-active agent added to the collagen or ECM materials) are substantially free of one or more of the following components: thrombin, non-autologous cellular components, active pepsin, and active virus. Such compositions can be prepared by treating the biomaterial, the structural member contained therein, or the solution for preparing the biomaterial/structural member to remove thrombin, DNA, DNA fragments, RNA and RNA fragments, cells, fragments of cell membrane, cell components, and/or to minimizes the incorporation of endotoxins or viruses. The biomaterials, structural members, and/or solutions for preparing such can also be treated to inactivate pepsin and remove/inactivate viruses. Such treatments can be performed following methods known in the art and/or those descried herein (see Examples 7 and 8 below).

For example, methods for removing cell components can involve the use of detergents, including SDS, EDTA, TritonX, polyethylene glyco, citrate, and sodium deoxycholate. These methods may also include the use of a surfactant. In addition, these methods may involve the use of enzymes, including trypsin, collagenase, elastase, DNAse and RNAse, ribonuclease, deoxyribonuclease, alpha-galactosidase, and other enzymes which can degrade cell membranes, receptors, or other cellular components. These methods may also include physical processes, including ultrasound, electron beam irradiation and gamma irradiation.

For each of these solutions containing one or more agents noted above, concentrations of solutions from 0.001% to 50% may be used. Preferred embodiments are for solutions in the range of 0.001 to 1.0%. Other preferred embodiments are for solutions in the range of 0.1 to 10.0%. Other solutions may be used in concentrations of IU/ml, for example, DNAse may be used in a concentration of 150 IU/ml.

In some examples, the pepsin in a biomaterial as described herein can be inactivated by bringing the pH of an ECM slurry such as a collagen slurry above 4.0 using a strong base such as NaOH or LiOH or KOH. Other bases include $Ba(OH)_2$ and $Sr(OH)_2$ can also be used to increase the pH of the solution and inactivate the pepsin. To inactivate the pepsin, a suitable volume of a suitable concentration of the strong base is added dropwise to the pepsin-containing slurry and the pH is recorded. This process is repeated until the pH of the slurry is above 4.0. Alternatively, the exact amount of the strong base that needs to be added is calculated based on the hydrogen ion content in the volume of slurry that needs to be counteracted by the strong base to raise the pH of the solution significantly and then that exact volume is measured and the pH is checked to ensure it is above 4.0. In other embodiments, the process is done in either of these two ways, but additional strong base is added until the pH reaches 6.0. In other embodiments, the process is done in either of these two ways, but additional strong base is added until the pH reaches 7.0 or greater. In other embodiments, the process is done in either of these two ways, but additional strong base is added until the pH reaches 8.0 or greater. In other embodiments, the process is done in either of these two ways, but additional strong base is added until the pH reaches 9.0 or greater. In other embodiments, the process is done in either of these two ways, but additional strong base is added until the pH reaches 10.0 or greater. In other embodiments, the process is done in either of these two ways, but additional strong base is added until the pH reaches 11.0 or greater. In other embodiments, the process is done in either of these two ways, but additional strong base is added until the pH reaches 5.0 or greater.

Once the slurry reaches its target pH range, the solution is kept there for a specific amount of time. This time may be between 10 seconds and 1 week. In a preferred embodiment, the time is between 1 and 10 minutes. In another preferred embodiment, the time is between 10 and 30 minutes. In another preferred embodiment, the time is between 10 and 60 minutes.

After inactivation of the pepsin, the pH of the slurry is returned to a pH between 7.0 and 8.0 by the addition of a buffer with a pK of between 7 and 8, such as a buffer containing TAPSO, HEPES, TES, MOPS, Cacodylate SSC or Succinic acid. Alternatively, phosphate buffered saline may be used, or $K_2HPO_4$. Any combination of a weak acid and its conjugate base, or a weak base and its conjugate acid may be used. A buffer of carbonic acid and bicarbonate may also be used. Blood or plasma containing carbonic acid and bicarbonate may be used. A universal buffer, such as that using citric acid and Na2HPO4 (McIlvaine's buffer solutions) may also be used in proportions that yield a buffer range of pH between 7 and 8.

Upon treatment as described above, the biomaterial described herein is substantial free of one or more of nucleic acid (DNA and/or RNA), glycosaminoglycan (GAG), phospholipid, active pepsin, and active virus. In some examples, the nucleic acid and/or phospholipid content in the biomaterial (e.g., dry weight) described herein is less than 20% of that in a native tissue such as dermis (e.g., less than 15%, 10%, 5%, or 1%). In other examples, the content of GAG in the biomaterial is less than 50% (e.g., 40%, 30%, 20%, 15%, 10%, or 5%) of the total dry weight of the biomaterial. In other examples, the level of active pepsin in the biomaterial described herein is less than 1000 ug/ml, e.g., less than 500 ug/ml, 200 ug/ml, or 100 µg/ml.

In some examples, viruses can be inactivated by ethylene oxide sterilization, e-beam sterilization, or gamma irradiation.

Medical Uses of Biomaterials

The biomaterials described herein, including collagen materials such as collagen gels and collagen sponges, and ECM scaffolds, can be used to prevent and/or minimize progression of injuries to the anterior cruciate ligament, the meniscus, labrum, cartilage, and other tissues exposed to synovial fluid after injury. They also can be used to alleviate and/or reduce the risk for developing arthritis (e.g., osteoarthritis), such as post-traumatic arthritis.

In some embodiments, the biomaterials described herein (e.g., the ECM scaffolds such as collagen scaffolds) are designed for use in an arthroscopic surgery with arthroscopic equipment. The scaffold can be compressible to allow introduction through arthroscopic portals and equipment. When desired, the scaffold can also be pre-treated in antibiotic solution or sterilization via a routine method prior to implantation. When a collagen-based scaffold is used in the treatment described herein, the affected extremity is prepared and draped in the standard sterile fashion. A tourniquet may be used if indicated. Standard arthroscopy equipment may be used. After diagnostic arthroscopy is performed, and an intra-articular lesion identified and defined, tissues desired for protection are pretreated, either mechanically or chemically, and the scaffold introduced into the joint. The scaffold is then bonded to the surrounding tissue by creating chemical or mechanical bonds between the tissue proteins and the scaffold biologic agent. This can be done by the addition of a chemical agent or a physical agent such ultraviolet light, a laser, or heat, the scaffold may be reinforced by placement of sutures or clips. The arthroscopic portals can be closed and a sterile dressing placed. The post-operative rehabilitation is dependent on the joint affected, the type and size of lesion treated, and the tissue involved.

EXAMPLES

Example 1: Terminal Sterilization Study

Methods: In this study, an extracellular matrix (ECM) scaffold prepared according to the methods of the invention was terminally sterilized using standard E-beam and EO sterilization. Briefly, the scaffolds were prepared by lyophilizing bovine connective tissue, washing the tissue, digesting in pepsin and then lyophilizing in a mold to make a cylindrical scaffold. The samples were placed inside glass vials. The glass vials were purged by Nitrogen in order to reduce the amount of the oxygen in them. The glass vials were then sealed and clamped as shown in FIG. 1 and stored on dry ice throughout the sterilization procedure.

E-Beam: For the e-beam groups, the ECM scaffolds were placed in glass vials that were capped and sealed using plastic stoppers and crimped using an aluminum clamping system. The samples were then subjected to 15 kGy E-Beam sterilization process by Sterigenics (San Diego, Calif.). An "e-beam" control group of scaffolds was shipped to Sterigenics but not sterilized and shipped back for testing.

The following conditions were used in the study for the 15 kGy E-beam process:

1. Temperature; sterilization under frozen condition on dry ice
2. Presence of Oxygen; the vial containing ECM Scaffold will be free of oxygen (Nitrogen purged)
3. Dosage; 15 kGy The packaging of the samples was similar to the image shown in FIG. 1; glass vials with rubber stoppers which will be sealed on top via aluminum sealing system.

EO: For the ethylene oxide groups, lyophilized ECM scaffolds were placed into gas permeable pouches and subjected to EO sterilization. The Ethylene concentration used was 735 mg/l for at least 4.75 hours. Each pouch was marked with the EO sterilization indicator to confirm the EO sterilization. The packaging of the samples was similar to image shown in FIG. 1.

Table 1 provides a summary of the study design.

TABLE 1

Study design for ECM scaffold sterilization using E-Beam and EO sterilization.

| Condition | # of Samples | ID | E-Beam Dose [kGy] | Outcome Measure |
|---|---|---|---|---|
| Sterile process ECM Scaffold in sealed glass vial, purged by nitrogen, frozen, and subjected to E-Beam sterilization while kept on dry ice during sterilization | 3 of OD = 22 mm Length = 30 mm | 1, 2, 3 | 15 | 1. Culture in media in an incubator for 7 days (n = 6; two from each scaffold). Cut 2 mm length from the bottom of each scaffold prior to other testing) 2. Passage a straight Keith needle through the scaffold in four parallel places without the |

TABLE 1-continued

Study design for ECM scaffold sterilization using E-Beam and EO sterilization.

| Condition | # of Samples | ID | E-Beam Dose [kGy] | Outcome Measure |
|---|---|---|---|---|
| | | | | scaffold fracturing (n = 3; prior to all tests except culture samples removed for #1 before this step) 3. Resistance to digestion by collagenase, elastase and plasmin able to (n = 6; two new samples from each scaffold) 4. A 22 mm dia × 10 mm length of ECM scaffold able to absorb 3cc of blood (n = 3) |
| Sterile-processed ECM Scaffold in sealed glass vial, purged by nitrogen, frozen shipped on dry ice to the sterilization facility and back, similar to top row samples. | 3 of OD = 22 mm Length = 30 mm | 4, 5, 6 | N/A | 1. Culture in media in an incubator for 7 days (n = 6; two from each scaffold). Cut 2 mm length from the bottom of each scaffold prior to other testing) 2. Passage a straight Keith needle through the scaffold in four parallel places without the scaffold fracturing (n = 3; prior to all tests except culture samples removed for #1 before this step) 3. Resistance to digestion by collagenase, elastase and plasmin able to (n = 6; two new samples from each scaffold) 4. A 22mm dia × 10 mm length of ECM scaffold able to absorb 3cc of blood (n = 3) |
| Sterile-processed ECM Scaffold samples kept at CHB | 3 of OD = 22 mm Length = 30 mm | 7, 8, 9 | N/A | 1. Culture in media in an incubator for 7 days (n = 6; two from each scaffold). Cut 2 mm length from the bottom of each scaffold prior to other testing) 2. Passage a straight Keith needle through the scaffold in four parallel places without the scaffold fracturing (n = 3; prior to all tests except culture samples removed for #1 before this step) 3. Resistance to digestion by collagenase, elastase and plasmin able to (n = 6; two new samples from each scaffold) 4. A 22mm dia × 10 mm length of ECM scaffold able to absorb 3cc of blood (n = 3) |
| ECM Scaffold packaged as shown in FIG. 1 and subjected to EO sterilization | 3 of OD = 22 mm Length = 30 mm | 10, 11, 12 | Low-temp EO | 1. Culture in media in an incubator for 7 days (n = 6; two from each scaffold). Cut 2 mm length from the bottom of each scaffold prior to other testing) 2. Passage a straight Keith needle through the scaffold in four parallel places without the scaffold fracturing (n = 3; prior to all tests except culture samples removed for #1 before this step) 3. Resistance to digestion by collagenase, elastase and plasmin able to (n = 6; two new samples from each scaffold) 4. A 22 mm dia × 10 mm length of ECM scaffold able to absorb 3 cc of blood (n = 3) |

Following the sterilization processes, the ECM Scaffold was subjected to a series of tests alongside the control non-sterile ECM Scaffold to determine whether the sterilization process caused any changes to the ECM Scaffold characteristics. The test included:

1) The scaffolds were incubated in culture in media for 7 days. No antibiotics were included in the media. The samples used for the culture test were cut in a laminar hood using sterile technique before any manipulation on the samples. A disc of 1 to 2 mm thickness was enough for each samples.

2) Passage of a straight Keith needle through the scaffold in four parallel places by hand and assessing any scaffold fracturing.

3) Collagenase digestion (250 ug/ml in PBS) times of 24 to 48 hours, Elastase digestion (100 μg/ml in PBS) times of 14 to 21 days, and Plasmin Digestion (40 ug/ml in water) digestion times of 7 to 14 days. One ml of enzyme solution will be used for each sample in separate wells of a 6 well plate. This is assuming the control non-sterilized ECM scaffold has times of 24 hours, 14 days and 7 days for collagenase, elastase and plasmin respectively. Sample size for each digestion assay was 8 mm diam, 7 mm height created by making a 7 mm slice of the larger scaffolds and then using an 8 mm sterile punch to get individual samples.

4) Absorption of blood; a 22 mm diameter×10 mm length of ECM scaffold should be able to absorb 3 cc of blood.

Results: The results obtained from the sterilized samples were compared to those obtained from the non-sterilized ECM Scaffold and control samples.

1. Culture Study:

4 out of six of the sterile processed control scaffolds showed a color change in the media after 14 days. The terminal sterilized specimens did not show any change. None of the wells had any growth of bacteria or fungus after 14 days that was grossly visible. No organisms were visible with microscopic examination of the culture wells for any of the scaffolds. The results demonstrate the efficacy of the sterilization techniques.

2. Keith Needle Study:

The panels are shown from left to right as follows: Ebeam/Ebeam Control/EO/Control. All four scaffolds showed no signs of breakage.

3. Enzyme Degradation Study:

In each instance, the scaffolds sterilized using Ebeam had slightly faster digestion rates. In general all the samples were very resistant.

4. Blood Absorption Study:

Absorption time was significantly prolonged in the EO group. All groups absorbed the total of 1 ml of whole blood. Loss of height during absorption was increased in the Ebeam group.

Gross Appearance: The Ebeam scaffolds showed a slight yellow discoloration. Whereas the control Ebeam scaffolds had no change. The EO scaffold had very slight yellow discoloration. From left to right: Ebeam/Ebeam Control/EO/Control.

Example 2: Evaluation of DNA Content/RNA Content/Cell Fragment Content in Scaffolds Scaffold were treated with various chemicals and enzymes to lower the DNA, GAG and Phospholipid content. As described in detail below it was possible to significantly reduce the DNA, GAG and Phospholipid content of the scaffolds.

In this experiment, tissues from 8 bovine knees were collected. The total wet weight of the harvested tissues was 166.5 g. The tissues were lyophilized until dry and then homogenized. The homogenized tissue was then divided into 16 samples with dry weights. The dry tissue samples were then rinsed in 2% antibiotic solution overnight.

Start of Differentiation:

Following the antibiotic rinse, the samples were divided into 16 different treatment groups as noted below.

Summary of Sample Groups: Differences Only are Noted in Table 2.

Sample 1: The tissue was rinsed with NaCl solution followed by ultrapure water three times, and then washed with citrate buffer with a pH=4.0 for 72 hours. The samples were ultracentrifuged and treated with pepsin and 0.01NHCl. The amount of pepsin and HCl was determined using the wet weight of the sample. The remaining sample was tested.

The tissue was rinsed with NaCl solution followed by ultrapure water three times. The samples were ultracentrifuged and treated with pepsin and HCl. The amount of pepsin and HCl was determined using the wet weight of the sample. The remaining sample was tested.

Sample 3: The tissue was rinsed with NaCl solution followed by ultrapure water. The sample was then treated with sterile RNase A (100 μg/mL) and DNase I (150 IU/mL) with 10 mmolMgCl2, in 0.05M Tris-Buffer (pH=7.5) and then washed with citrate buffer with a pH=4.0 for 72 hours. The tissue was then again rinsed with NaCl solution. The samples were ultracentrifuged and treated with pepsin and HCl. The amount of pepsin and HCl was determined using the wet weight of the sample. The remaining sample was tested.

Sample 4: The tissue was rinsed with NaCl solution followed by ultrapure water. The sample was then treated with sterile RNase A (100 μg/mL) and DNase I (150 IU/mL) with 10 mmolMgCl2, in 0.05M Tris-Buffer (pH=7.5). The tissue was then again rinsed with NaCl solution. The samples were ultracentrifuged and treated with pepsin and HCl. The amount of pepsin and HCl was determined using the wet weight of the sample. The remaining sample was tested.

Sample 5: The tissue was rinsed NaCl solution followed by ultrapure water. The sample was then treated with sterile RNase A (100 μg/mL) and DNase I (150 IU/mL) with 10 mmolMgCl2, in 0.05M Tris-Buffer (pH=7.5) and then washed with citrate buffer with a pH=4.0 for 72 hours. The samples were ultracentrifuged and treated with pepsin and HCl. The amount of pepsin and HCl was determined using the wet weight of the sample. The remaining sample was tested.

Sample 6: The tissue was rinsed with NaCl solution followed by ultrapure water. The sample was then treated with sterile RNase A (100 μg/mL) and DNase I (150 IU/mL) with 10 mmolMgCl2, in 0.05M Tris-Buffer (pH=7.5). The samples were ultracentrifuged and treated with pepsin and HCl. The amount of pepsin and HCl was determined using the wet weight of the sample. The remaining sample was tested.

Sample 7: The tissue was rinsed with ultrapure water. The sample was then treated with sterile RNase A (100 μg/mL) and DNase I (150 IU/mL) with 10 mmolMgCl2, in 0.05M Tris-Buffer (pH=7.5) and then washed with citrate buffer with a pH=4.0 for 72 hours. The tissue was then again rinsed with NaCl solution. The samples were ultracentrifuged and treated with pepsin and HCl. The amount of pepsin and HCl was determined using the wet weight of the sample. The remaining sample was tested.

Sample 8: The tissue was rinsed with ultrapure water. The sample was then treated with sterile RNase A (100 µg/mL) and DNase I (150 IU/mL) with 10 mmolMgCl2, in 0.05M Tris-Buffer (pH=7.5). The tissue was then again rinsed with NaCl solution. The samples were ultracentrifuged and treated with pepsin and HCl. The amount of pepsin and HCl was determined using the wet weight of the sample. The remaining sample was tested.

Sample 9: The tissue was rinsed with ultrapure water. The sample was then treated with sterile RNase A (100 µg/mL) and DNase I (150 IU/mL) with 10 mmolMgCl2, in 0.05M Tris-Buffer (pH=7.5) and then washed with citrate buffer with a pH=4.0 for 72 hours. The samples were ultracentrifuged and treated with pepsin and HCl. The amount of pepsin and HCl was determined using the wet weight of the sample. The remaining sample was tested.

Sample 10: The tissue was rinsed with ultrapure water. The sample was then treated with sterile RNase A (100 µg/mL) and DNase I (150 IU/mL) with 10 mmolMgCl2, in 0.05M Tris-Buffer (pH=7.5). The samples were ultracentrifuged and treated with pepsin and HCl. The amount of pepsin and HCl was determined using the wet weight of the sample. The remaining sample was tested.

Sample 11: The sample was treated with sterile RNase A (100 pg/mL) and DNase I (150 IU/mL) with 10 mmolMgCl2, in 0.05M Tris-Buffer (pH=7.5) and then washed with citrate buffer with a pH=4.0 for 72 hours. The tissue was then again rinsed with NaCl solution. The samples were ultracentrifuged and treated with pepsin and HCl. The amount of pepsin and HCl was determined using the wet weight of the sample. The remaining sample was tested.

Sample 12: The sample was treated with sterile RNase A (100 µg/mL) and DNase I (150 IU/mL) with 10 mmolMgCl2, in 0.05M Tris-Buffer (pH=7.5). The tissue was then again rinsed with NaCl solution. The samples were ultracentrifuged and treated with pepsin and HCl. The amount of pepsin and HCl was determined using the wet weight of the sample. The remaining sample was tested.

Sample 13: The sample was treated with sterile RNase A (100 pg/mL) and DNase I (150 IU/mL) with 10 mmolMgCl2, in 0.05M Tris-Buffer (pH=7.5) and then washed with citrate buffer with a pH=4.0 for 72 hours. The samples were ultracentrifuged and treated with pepsin and HCl. The amount of pepsin and HCl was determined using the wet weight of the sample. The remaining sample was tested.

Sample 14: The sample was treated with sterile RNase A (100 µg/mL) and DNase I (150 IU/mL) with 10 mmolMgCl2, in 0.05M Tris-Buffer (pH=7.5). The samples were ultracentrifuged and treated with pepsin and HCl. The amount of pepsin and HCl was determined using the wet weight of the sample. The remaining sample was tested.

Sample 15: The tissue was rinsed with NaCl solution followed by ultrapure water. The sample was then treated with TritonX-Sodium deoxycholate-PBS solution at 0 to 25 degrees C. for at least 24 hours. The tissue was rinsed and then treated with sterile RNase A (100 µg/mL) and DNase I (150 IU/mL) with 10 mmolMgCl2, in 0.05M Tris-Buffer (pH=7.5) and then washed with citrate buffer with a pH=4.0 for 72 hours. The samples were ultracentrifuged and treated with pepsin and HCl. The amount of pepsin and HCl was determined using the wet weight of the sample. The remaining sample was tested.

Sample 16: The tissue was rinsed with NaCl solution followed by ultrapure water. The sample was then treated with TritonX-Sodium deoxycholate-PBS solution at 0 to 25 degrees C. for at least 24 hours. The tissue was rinsed and then treated with sterile RNase A (100 µg/mL) and DNase I (150 IU/mL) with 10 mmolMgCl2, in 0.05M Tris-Buffer (pH=7.5). The samples were ultracentrifuged and treated with pepsin and HCl. The amount of pepsin and HCl was determined using the wet weight of the sample. The remaining sample was tested.

Figure 2:
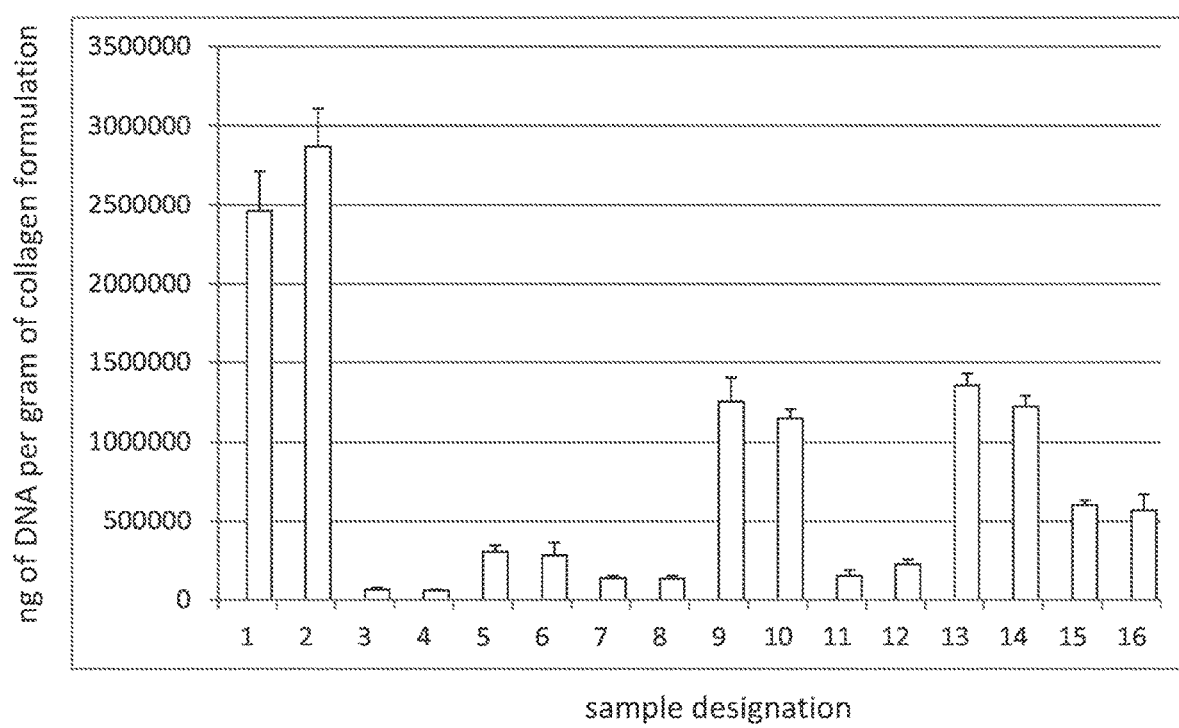
FIG. 2 is a chart showing DNA content in samples treated as described in Example 2 below.

DNA contents of the treated samples as described above were determined. As shown in FIG. 2, they axis is ng of DNA per gram of collagen formulation, and the x axis is the sample designation as noted above. These data show the relative efficacy of the citrate rinse (samples 4, 6, 11) and the DNAse/RNAse steps (samples 3, 4, 5, 6, 7, 8). Triton X also had some efficacy (Samples 15 and 16). For reference, the DNA content of the native tissue is approximately 500,000 to 3,000,000 ng DNA/g tissue.

The treated samples were compared with those in native tissues and in commercially available scaffolds, using the processing techniques described above. The collagen scaffold described herein was tested against: 1) native tissue, 2) Surgifoam, 3) TissueMend. Collagen content (FIG. 3, panel A), GAG content (FIG. 3, panel B), and phophatidylcholine content (FIG. 3, panel C) as a measure of retained cellular membrane were investigated. The results are listed below.

Figure 3A:
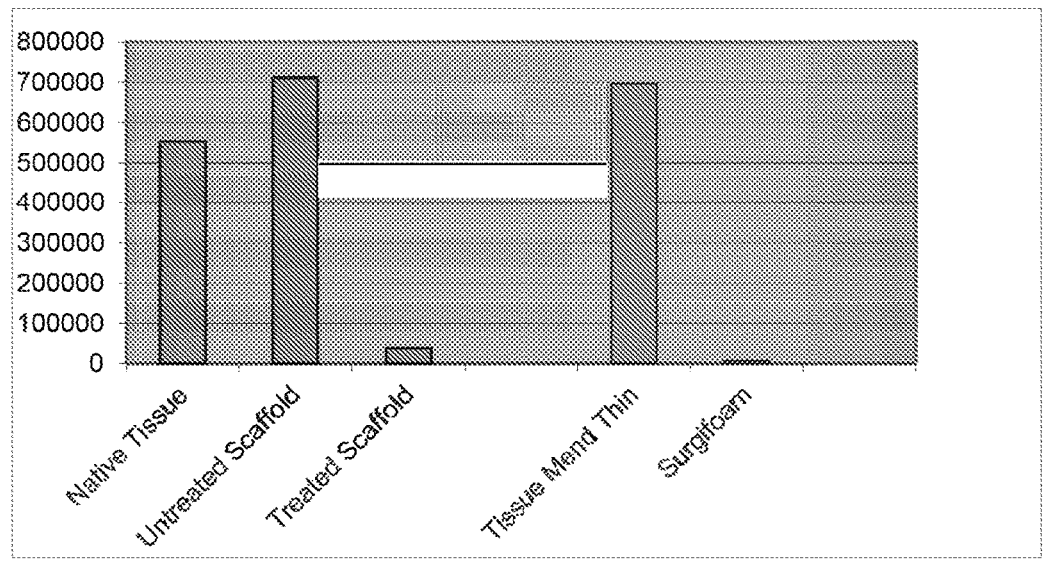
FIGS. 3A-3C depict DNA content (3A), GAG content (3B), and phospholipid content (3C) in samples treated as described in Example 2 below relative to the DNA, GAG, and phospholipid content in native tissues and in commercially available collagen scaffold.
Figure 3B:
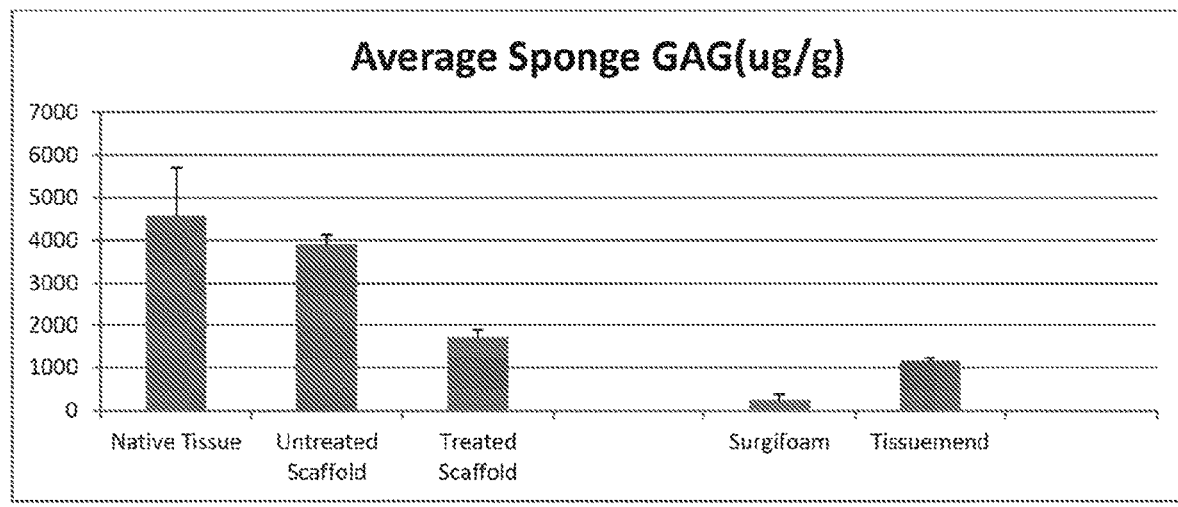
Figure 3C:
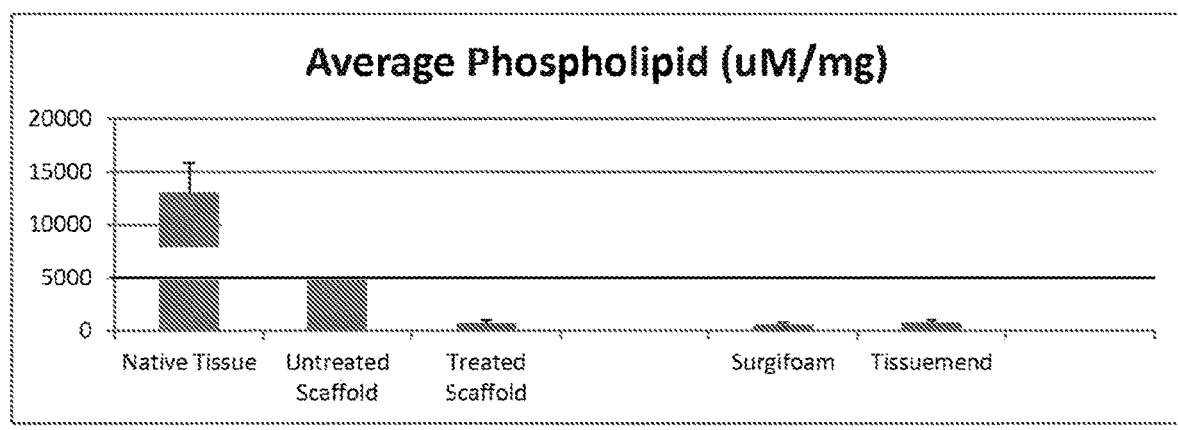

DNA content (ng DNA/g tissue or scaffold) for treated and untreated scaffolds was compared with that in native tissue (no treatment), TissueMend and Surgifoam (two FDA approved scaffolds). The treatment of the scaffold with techniques to remove DNAs as described above reduced the DNA content in the scaffold to less than 20% of that found in the native tissue. FIG. 3, panel A.

GAG content (ug GAG/g tissue or scaffold) for treated and untreated scaffolds was compared with that of native tissue (no treatment), TissueMend and Surgifoam (two FDA approved scaffolds). The treatment of the scaffold with techniques described above to remove the GAG reduced the GAG in the scaffold by over 30%. FIG. 3, Panel B.

Phospholipid content (uM/mg) of the native tissue, untreated scaffold and treated scaffold was compared with that in Surgifoam and TissueMend (two FDA approved scaffolds). The treatment of the scaffold with techniques described above to remove the phospholipid reduced the phospholipid in the scaffold to a level less than 20% that found in the native tissue. FIG. 3, panel C.

Example 3: Chemical Neutralization of the Pepsin Content in a Scaffold

Scaffolds were made from extracellular matrix proteins using a pepsin digestion. After digestion, one group had no further treatment, while the second group was treated with a chemical to inactivate the pepsin.

Scaffolds were made from extracellular matrix proteins using a pepsin digestion. After digestion, one group had no further treatment, while the second group was treated with a strong base to inactivate the pepsin.

Briefly, a strong base (e.g., KOH or NaOH or LiOH) at a suitable concentration was added into a collagen slurry in a dropwise manner to bring the pH value to above 4.0. Additional strong base was added to bring the pH of the slurry to 7.0 or greater. Once the slurry reached its target pH range, the solution is kept there for a suitable period of time, e.g., 1 to 10 minutes.

After inactivation of the pepsin, the pH of the slurry was returned to a pH between 7.0 and 8.0 by the addition of a buffer with a pK of between 7 and 8, such as a buffer containing TAPSO, HEPES, TES, MOPS, Cacodylate SSC or Succinic acid.

Figure 4:
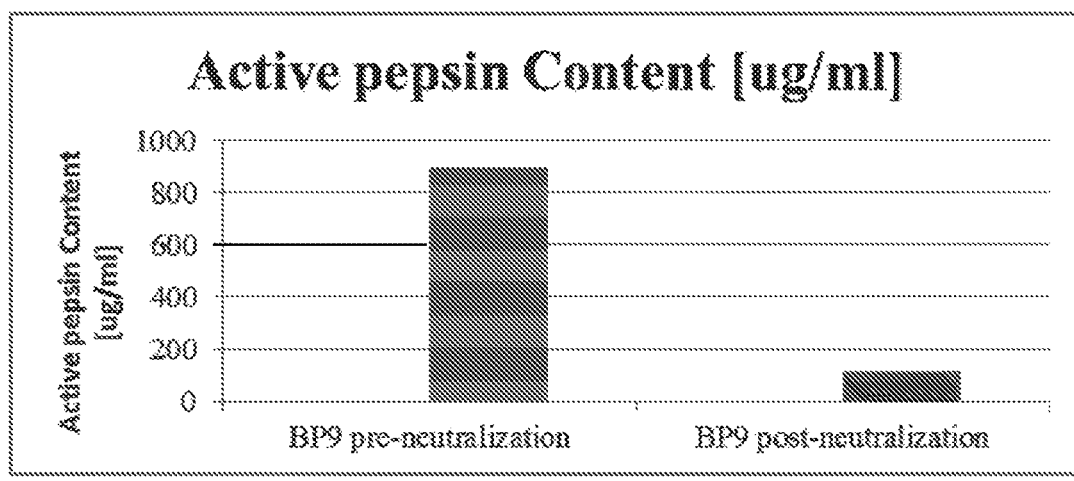
FIG. 4 is a chart showing the level of active pepsin in collagen materials treated as described in Example 3 below.

As shown in FIG. 4, the level of active pepsin in a collagen material reduced by around 80% as compared to the active pepsin level before the inactivation treatment.

Example 4: Testing Collagen Sponge with Calcium Added into Collagen Slurry

Methods: Five collagen sponges containing three different concentrations of CaCl2 (high, medium and low), were prepared. The sponges were prepared by taking collagen slurry, and adding a 30 mM, 60 mM or 90 mM solution. The slurry was then lyophilized. The sponges were then rehydrated with water to result in a specific collagen concentration. The collagen slurry was neutralized using a buffer with a pK of between 7 and 8 (Cellgro, Mediatech, Inc, Herndon, Va.) and enough 7.5% sodium bicarbonate (Cambrex BioScience Walkersville, Inc., Walkersville, Md.) to neutralize the acidic slurry to a pH of 7.4. Five 1.0 mL aliquots of the each concentration of neutral collagen gel was transferred into wells of a 24-wellplate and warmed until gelation occurred. The gels were then lyophilized to make the collagen-calcium sponges.

0.75 mL platelet-rich plasma (PRP) containing plasma, platelets and an anticoagulant was placed on two sponges of each type to see if a clot formed in the collagen-calcium sponge. Two sponges of each concentration were also compressed and then PRP containing an anticoagulant was added to see if that affected clot formation.

Results: After 10 minutes, clotting did occur in the 90 mM CaCl2 solution sponge. The lower calcium solutions did not clot as well, but some initial clotting did occur. It did not matter whether or not the sponge was compressed before PRP was added. The collagen sponges with calcium allowed the clot to form within the sponge at all concentrations of calcium, even when the blood components were drawn into a tube containing an anticoagulant. The collagen-calcium was able to cause clotting of the anticoagulated blood product in the absence of any added thrombin.

Example 5: Testing HDBC Sponge with Calcium and a Second Lyophilization

Method: To make the collagen sponges, acid soluble collagen slurry was lyophilized, and rehydrated with water to have a collagen concentration >10 mg/ml. The collagen slurry was neutralized using HEPES Buffer (Cellgro, Mediatech, Inc, Herndon, Va.) and sodium bicarbonate (Cambrex BioScience Walkersville, Inc., Walkersville, Md.) to neutralize the acidic slurry to a pH of 7.4. The pH neutral collagen gel was incubated at 37 degrees C. to allow for gelation of the collagen hydrogel and self-assembly of the collagen fibers, and the gel was then lyophilized to make a collagen sponge. The collagen sponge was cut into thirds and each third was placed into its own Petri dish. One sponge was covered with a low concentration solution of calcium, one sponge was covered with a medium concentration of calcium, and one sponge was covered with a high concentration of calcium. These three sponges were placed in new Petri dishes and were then placed back into the lyophilizer for three days.

The collagen sponges were removed from the lyophilizer and 0.75 mL of a solution containing an anticoagulant, platelet, plasma and white blood cells was placed on each sponge. After 10 minutes, the sponges were put into a 50 cc test tube, and shaken and vortexed to test their structural rigidity.

Results: It was found that a clot formed in each of the sponges within 10 minutes of the blood components being added. The collagen sponges with calcium allowed the clot to form within the sponge at all concentrations of calcium, even when the blood components were drawn into a tube containing an anticoagulant. The collagen-calcium was able to cause clotting of the anticoagulated blood product in the absence of any added thrombin.

The foregoing written specification is considered to be sufficient to enable one skilled in the art to practice the invention. The present invention is not to be limited in scope by examples provided, since the examples are intended as a single illustration of one aspect of the invention and other functionally equivalent embodiments are within the scope of the invention. Various modifications of the invention in addition to those shown and described herein will become apparent to those skilled in the art from the foregoing description and fall within the scope of the appended claims. The advantages and objects of the invention are not necessarily encompassed by each embodiment of the invention. Those skilled in the art will recognize or be able to ascertain using no more than routine experimentation, many equivalents to the specific embodiments of the invention described herein. Such equivalents are intended to be encompassed by the following claims.

All references disclosed herein are incorporated by reference in their entirety.

What is claimed:

1. A collagen implant configured to repair tissue exposed to synovial fluid, the collagen implant comprising:
    an implant body having a size and shape that is configured for implantation into an articular joint where synovial fluid is present, the implant body entirely comprised of a self-assembly of collagen fibers, the self-assembly of collagen fibers having calcium, and including less than about 50,000 ng/g of DNA, less than about 5,000 uM/g of phospholipids, less than about 2,000 ug/g of GAG, less than about 25 ug/g of nucleic acids, wherein the collagen fibers are Type I collagen, and wherein the implant body is expandable and compressible and is capable of absorbing at least 3 ml of blood and has resistance to degradation by synovial fluid.

2. The collagen scaffold implant of claim 1, wherein the Type I collagen is obtained from a bovine knee.

3. The collagen implant of claim 1, wherein the self-assembly of collagen fibers comprises atelocollagen.

4. The collagen implant of claim 1, wherein the self-assembly of collagen fibers further comprises a therapeutic protein.

5. The collagen implant of claim 1, wherein the implant body has a first end, a second end opposed to the first end, and an outer wall that forms a generally cylindrical shape.

6. The collagen implant of claim 1, wherein the implant is capable of absorbing at least 9 ml of blood.

7. The collagen implant of claim 1, wherein the implant body is configured to permit a suture to pass therethrough.

8. The collagen implant of claim 1, wherein the self-assembly of collagen fibers are substantially free of one or more of the following components: thrombin, non-autologous cellular components, active pepsin, and active virus.

9. The collagen implant of claim 7, wherein the implant body is configured to be indirectly coupled to an anchor via the suture.

10. The collagen implant of claim 1, wherein the collagen implant is a sponge.

11. The collagen implant of claim 1, wherein the implant body is 22 mm in diameter.

12. The collagen implant of claim 1, wherein the implant body is 30 mm in length.

13. The collagen implant of claim 1, wherein the self-assembly of collagen fibers include greater than 100 ug/g of GAG.

14. The collagen implant of claim 1, wherein the self-assembly of collagen fibers have a collagen concentration of greater than 10 mg/mL.

* * * * *